(12) United States Patent
Platzek et al.

(10) Patent No.: US 12,365,679 B2
(45) Date of Patent: Jul. 22, 2025

(54) PROCESS FOR PRODUCING ACYLOXYMETHYL ESTERS OF (4S)-(4-CYANO-2-METHOXYPHENYL)-5-ETHOXY-2,8-DIMETHYL-1,4-DIHYDRO-1,6-NAPHTHYRIDIN-3-CARBOXYLIC ACID

(71) Applicant: Bayer Aktiengesellschaft, Leverkusen (DE)

(72) Inventors: Johannes Platzek, Berlin (DE); Kai Lovis, Düsseldorf (DE); Alba Hernandez Martin, Düsseldorf (DE); Silja Brady, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 272 days.

(21) Appl. No.: 17/769,241

(22) PCT Filed: Oct. 12, 2020

(86) PCT No.: PCT/EP2020/078611
§ 371 (c)(1),
(2) Date: Apr. 14, 2022

(87) PCT Pub. No.: WO2021/074077
PCT Pub. Date: Apr. 22, 2021

(65) Prior Publication Data
US 2024/0150344 A1    May 9, 2024

(30) Foreign Application Priority Data
Oct. 17, 2019 (EP) ..................... 19203821

(51) Int. Cl.
| C07D 471/04 | (2006.01) |
| C07B 57/00 | (2006.01) |
| C12N 9/20 | (2006.01) |
| C12P 41/00 | (2006.01) |

(52) U.S. Cl.
CPC ............ *C07D 471/04* (2013.01); *C07B 57/00* (2013.01); *C12N 9/20* (2013.01); *C12P 41/00* (2013.01); *C07B 2200/07* (2013.01); *C12Y 301/01003* (2013.01)

(58) Field of Classification Search
None
See application file for complete search history.

(56) References Cited

U.S. PATENT DOCUMENTS

| 5,234,821 A | 8/1993 | Achiwa |
| 8,436,180 B2 | 5/2013 | Barfacker et al. |
| 10,059,707 B2 | 8/2018 | Platzek et al. |
| 10,392,384 B2 * | 8/2019 | Platzek ..................... C25B 3/25 |
| 2014/0275042 A1 | 9/2014 | Verdecia Reyes et al. |

FOREIGN PATENT DOCUMENTS

| CN | 106279000 A | 1/2017 |
| WO | 2008104306 A2 | 9/2008 |
| WO | 2016016287 A1 | 2/2016 |

OTHER PUBLICATIONS

Baldaro, E. et al., "Phenylacetyloxymethylene, a Carboxyl Protecting Group Removable with Immobilized Penicillin Acylase, Useful in Benzyl Penicillin Chemistry," Tetrahedron Letters 1988, 29(36), 4623-4624.
Bärfacker, L. et al., "Discovery of BAY 94-8862: A Nonsteroidal Antagonist of the Mineralcorticoid Receptor for the Treatment of Cardiorenal Diseases," Chem Med Chem 2012, 7, 1385-1403.
Fuganti, C. et al., "Selective Transformations of Penicillins and Cephalosporins with Pen G Acylase," Biotechnology Letters, 1994, 16(9), 919-922.
International Search Report of PCT/EP2020/078611 (filed on Oct. 12, 2020 by Bayer Aktiengesellschaft); international search completed on Nov. 9, 2020; mailed on Nov. 23, 2020 by the European Patent Office; 15 pages.
Mustafaev, N.P. et al., "Synthesis of Acyloxyalkyl Esters of Thiocarbonic and Dithiocarbamic Acids," RU J. Org. Chem. 2013, 49(2), 198-203.
Paredes, G. et al., "Optimization of stimulated moving bed and column chromatography for a plasmid DNA purification step and for a chiral separation," Journal of Chromatography A 2007, 1142, 56-68.
Schnell, B. et al., "Synthesis and reactions of Biginelli-compounds. Part 23. Chemoenzymatic syntheses of enantiomerically pure 4-aryl-3,4- dihydropyrimidin-2(1H)-ones," J. Chem. Soc., 2000, Perkin Trans. 1, 4382-4389.
Sobolev, A. et al., "Candida rugosa Lipase-Catalyzed Kinetic Resolution of 3-(Isobutyryloxy)Methyl 4-[2- (Difluoromethoxy)Phenyl]-2-Methyl-5,5-Dioxo-1,4-Dihydrobenzothieno-[3,2-b]Pyridine-3-Carboxylate," Chemistry of Heterocyclic Compounds, 2004, 40(7), 931-937.
Sobolev, A. et al., "Chemoenzymatic Synthesis of Enantiopure 1,4-Dihydropyridine Derivatives," Biocatalysis and Biotransformation, 2004, 22(4), 231-252.
Sosnovsky, G. et al., "Synthesis of Nitroxyl (Aminoxyl) Labeled Probes for Studies of Intracellular Environment by EPR and MRI," J Org. Chem. 1989, 54(15), 3667-3674.

(Continued)

*Primary Examiner* — Kortney L. Klinkel
*Assistant Examiner* — Donna M Nestor
(74) *Attorney, Agent, or Firm* — Quarles & Brady LLP

(57) ABSTRACT

The present invention relates to a process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa) by optical resolution of the compound of the formula (II) using a hydrolase. The invention also relates to a process for preparing (4S)-4-(4-cyano-2-methoxyphenyl)-5-ethoxy-2,8-dimethyl-1,4-dihydro-1,6-naphthyridine-3-carboxamide of the formula (Ia), wherein the process comprises the optical resolution of the compound of the formula (II) using a hydrolase. The invention additionally also relates to the use of a hydrolase in a process for preparing a compound of formula (IIa). The invention further relates to the use of a hydrolase in a process for preparing a compound of formula (Ia).

15 Claims, No Drawings

(56) References Cited

OTHER PUBLICATIONS

Subramani, H.J. et al., "Optimization of reactive SMB and Varicol systems," Computers and Chemical Engineering 2003, 27, 1883-1901.
Torres, S.Y. et al., "Chemoenzymatic approach to optically active 1,4-dihydropyridine derivatives," Tetrahedron 2015, 71, 3976-3984.
Torres, S.Y. et al., "Chemoenzymatic synthesis of optically active phenolic 3,4-dihydropyridin-2-ones: a way to access enantioenriched 1,4-dihydropyridine and benzodiazepine derivatives," Org. Biomol. Chem. 2017, 15, 5171-5181.

\* cited by examiner

PROCESS FOR PRODUCING ACYLOXYMETHYL ESTERS OF (4S)-(4-CYANO-2-METHOXYPHENYL)-5-ETHOXY-2,8-DIMETHYL-1,4-DIHYDRO-1,6-NAPHTHYRIDIN-3-CARBOXYLIC ACID

The present invention relates to a process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa) by optical resolution of the compound of formula (II) using a hydrolase:

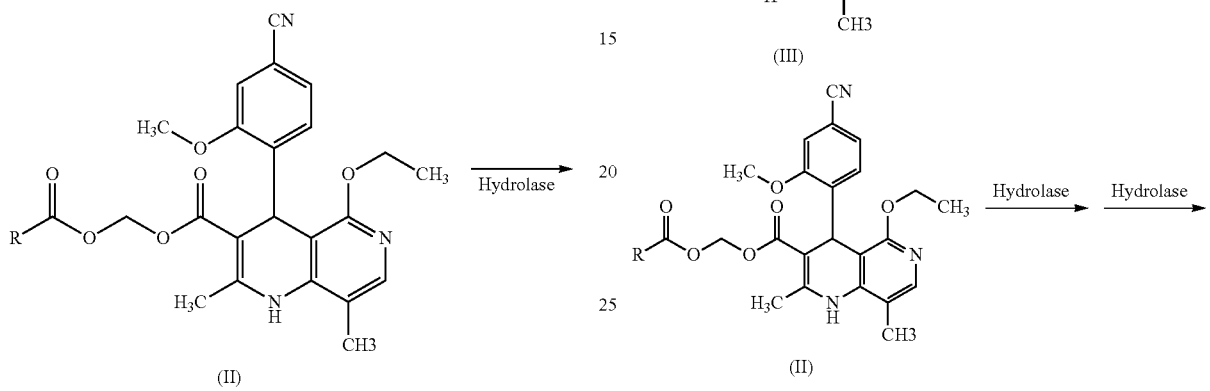

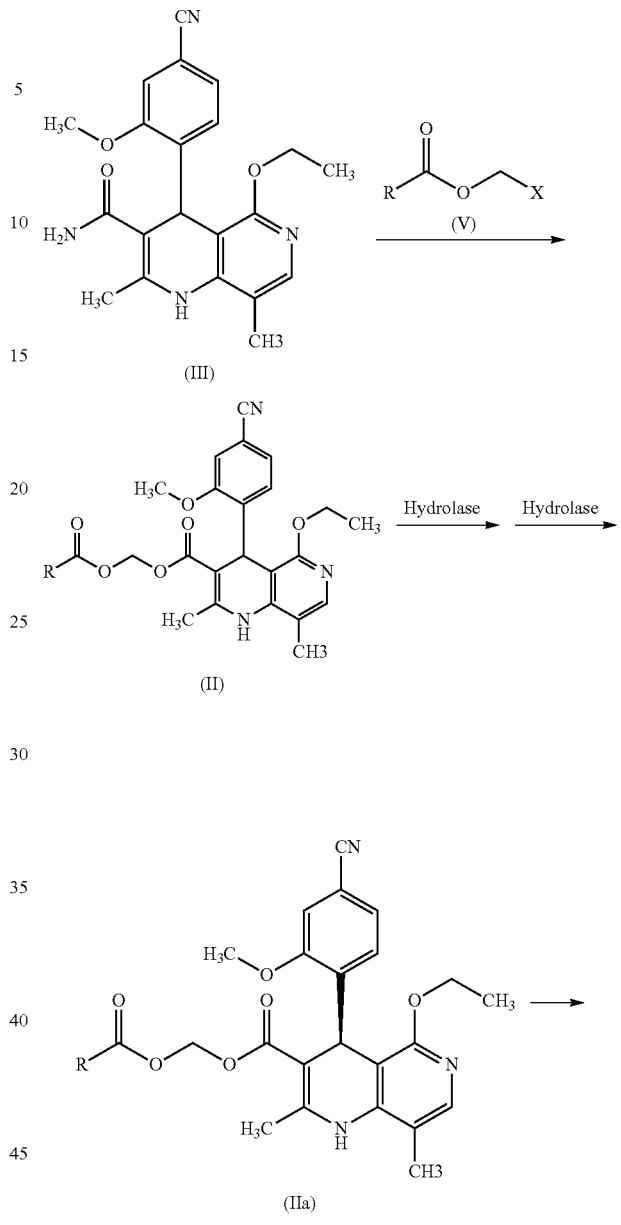

The invention also relates to a process for preparing (4S)-4-(4-cyano-2-methoxyphenyl)-5-ethoxy-2,8-dimethyl-1,4-dihydro-1,6-naphthyridine-3-carboxamide of the formula (Ia), wherein the process comprises the optical resolution of the compound of the formula (II) using a hydrolase.

The invention further relates to a process for preparing (4S)-4-(4-cyano-2-methoxyphenyl)-5-ethoxy-2,8-dimethyl-1,4-dihydro-1,6-naphthyridine-3-carboxamide of the formula (Ia), wherein the racemic acid of the formula (III) is reacted with halo esters of the general formula (V) to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II), and the latter is converted by optical resolution using a hydrolase to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa), and the latter is hydrolysed to the compound of the formula (IIIa) and this compound of the formula (IIIa) is then converted so as to obtain the compound of formula (Ia):

-continued

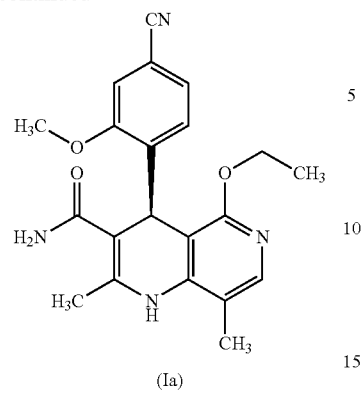

(Ia)

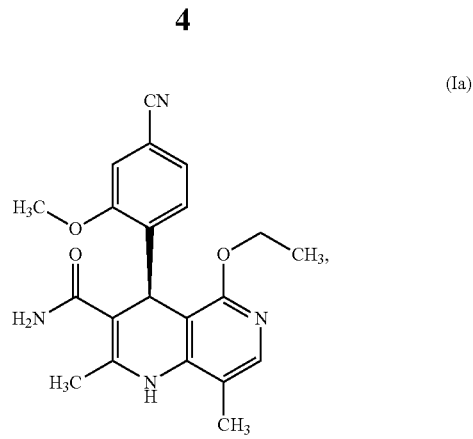

(Ia)

More particularly, the present invention relates to a process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

wherein the racemic acid of the formula (III)

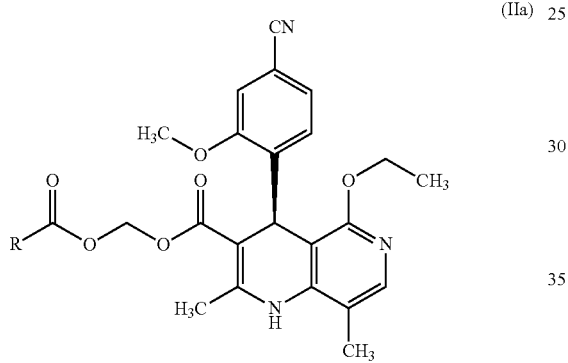

(IIa)

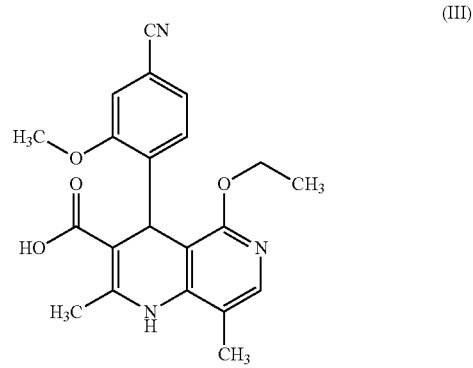

(III)

where R is a linear or branched C1-C25 chain optionally substituted by an aromatic radical, by optical resolution of the compound of formula (II)

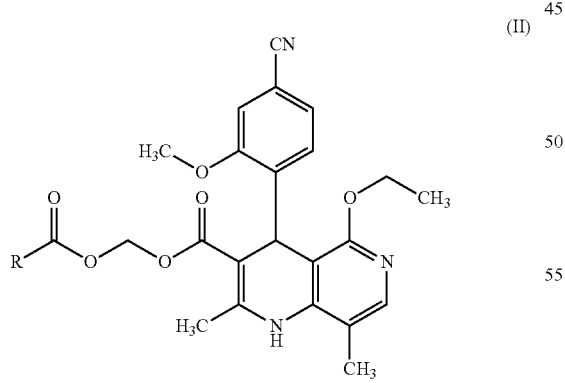

(II)

is reacted with halo esters of the general formula (V)

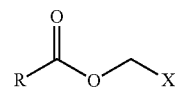

(V)

where R is a linear or branched C1-C25 chain, using a hydrolase.

The invention relates more particularly to a process for preparing (4S)-4-(4-cyano-2-methoxyphenyl)-5-ethoxy-2,8-dimethyl-1,4-dihydro-1,6-naphthyridine-3-carboxamide of the formula (Ia)

where

R is a linear or branched C1-C25 chain optionally substituted by an aromatic radical, X is chlorine or bromine, to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

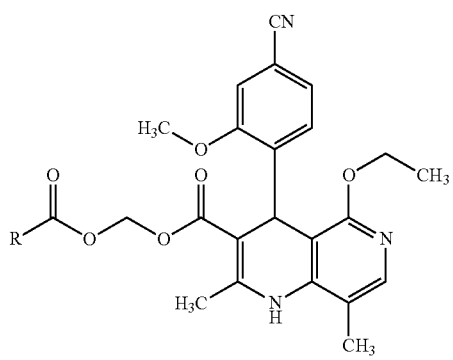

(II)

where R is a linear or branched C1-C25 chain optionally substituted by an aromatic radical,
and this is converted by optical resolution using a hydrolase
to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

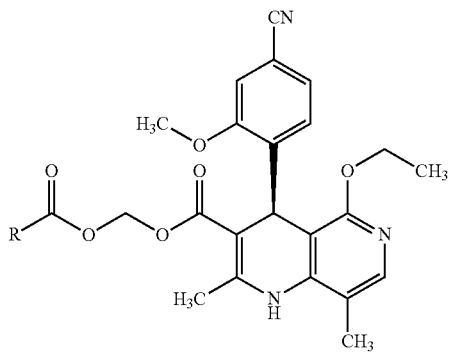

(IIa)

where R is a linear or branched C1-C25 chain optionally substituted by an aromatic radical,
and this is hydrolysed in a THF/water mixture (2:1) with sodium hydroxide solution to give the compound of the formula (IIIa)

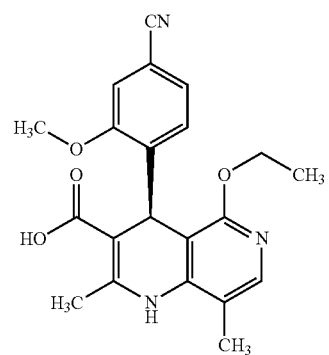

(IIIa)

and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

The invention additionally also relates to the use of a hydrolase in a process for preparing a compound of formula (IIa).

The invention also relates to the use of a hydrolase in a process for preparing a compound of formula (Ia). The term "finerenone" relates to the compound (4S)-4-(4-cyano-2-methoxyphenyl)-5-ethoxy-2,8-dimethyl-1,4-dihydro-1,6-naphthyridine-3-carboxamide or to the compound of formula (Ia)

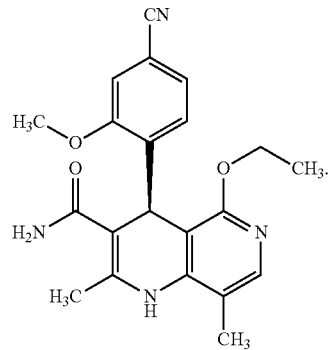

(Ia)

The compound of the formula (I)

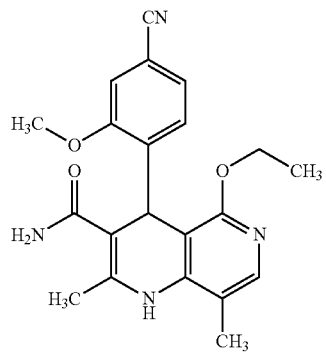

(I)

is the racemate of finerenone.

The expression "antipodes of finerenone" or "antipodes of the compound of formula (I)" concerns the compounds of formulae (Ia) and (Ib)

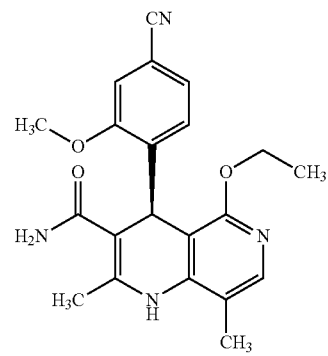

(Ia)

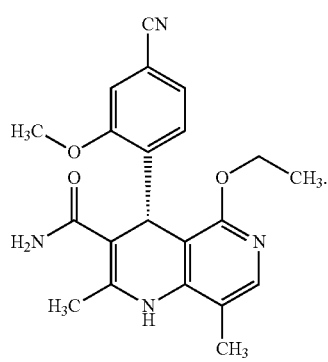
(Ib)

Finerenone (Ia) acts as a nonsteroidal antagonist of the mineralocorticoid receptor and can be used as an agent for prophylaxis and/or treatment of cardiovascular and renal disorders such as heart failure and diabetic nephropathy.

The compound of the formula (Ia) and the preparation process therefor are described in WO 2008/104306 A1 and ChemMedChem 2012, 7, 1385, and also in WO 2016/016287 A1. In order to arrive at the compound of the formula (Ia), the racemic mixture of the amides (I)

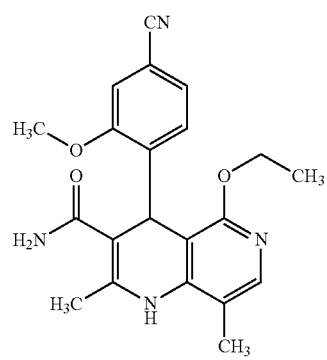
(I)

has to be separated into the antipodes (Ia) and (Ib)

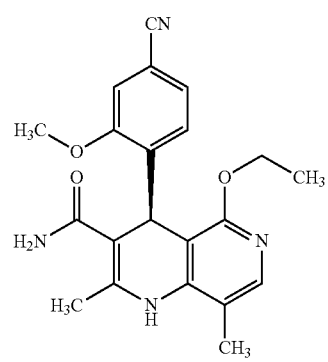
(Ia)

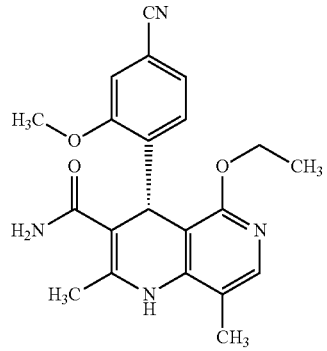
(Ib)

since only the antipode of the formula (Ia)

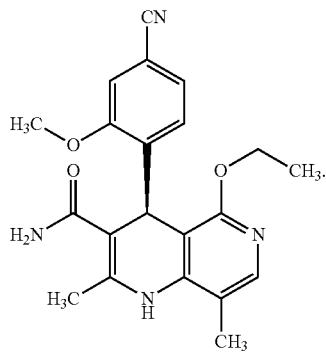
(Ia)

is active.

In the published research scale synthesis (WO 2008/104306 A1), a specifically synthesized chiral phase was used for this purpose (prepared in-house), which contained N-(dicyclopropylmethyl)-N²-methacryloyl-D-leucinamide as chiral selector. It has been found that the separation can also be performed on a readily commercially available phase. This is the Chiralpak AS-V phase, 20 m. The eluent used was a mixture of methanol/acetonitrile 60:40. In this case, the chromatography can be conducted on a conventional chromatography column, but preference is given to using techniques known to those skilled in the art such as SMB (simulated moving bed; G. Paredes, M. Mazotti, Journal of Chromatography A, 1142 (2007): 56-68) or Varicol (Computers and Chemical Engineering 27 (2003) 1883-1901).

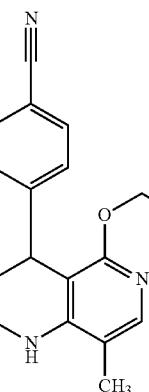

1) chiral HPLC
2) EtOH crystallization (I) racemic

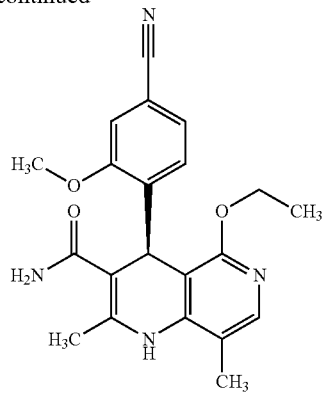

(Ia)

Although SMB separation affords a relatively good yield and optical purity, the procurement costs and the operation of such a facility under GMP conditions poses a great challenge and is associated with high costs. Even the chiral phase used in each case is very expensive and has only a limited lifespan and has to be replaced time and again in the course of production. For reasons of production engineering, this is not optimal unless there is a second facility to ensure continuous operation, which is associated with additional costs. Furthermore, especially in the case of products produced on a ton scale, solvent recovery is the time-limiting step and requires the procurement of huge falling-film evaporators and is associated with the consumption of enormous amounts of energy.

The problem addressed was therefore that of providing an alternative synthetic route to enantiomerically pure finerenone (Ia) that is significantly less costly and can be performed with conventional pilot plant equipment (stirred tanks/isolation apparatuses). Such facilities are traditionally standard equipment of pharmaceutical production plants and do not require additional investments. Moreover, qualification and validation of batch processes is considerably easier than that of chromatographic processes, which is an additional advantage.

The present invention relates to a process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

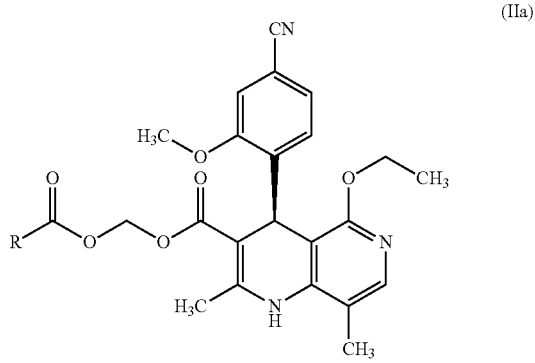

(IIa)

where R is a linear or branched C1-C25 chain, by optical resolution of (II)

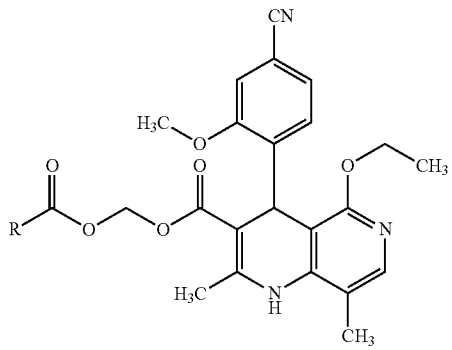

(II)

where R is a linear or branched C1-C25 chain, using a hydrolase.

The expression "C1-C25 chain" means a "$C_1$-$C_{25}$-alkyl chain". The expression "$C_1$-$C_{25}$-alkyl" means a linear or branched saturated monovalent hydrocarbyl group having 1, 2, 3, 4, 5, 6, 7, 8, 9, 10, 11, 12, 13, 14, 15, 16, 17, 18, 19, 20, 21, 22, 23, 24 or 25 carbon atoms. Examples of alkyl groups usable in accordance with the invention are methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neopentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group or an isomer thereof.

The C1-C25 chain may be linear or branched.

The C1-C25 chain may be substituted by an aromatic radical.

The term "substituted" means that one or more hydrogen atoms on the atom or group in question has/have been replaced by a selection from the group specified, with the proviso that the normal valency of the atom in question is not exceeded under the particular circumstances. Combinations of substituents and/or variables are permissible.

The term "unsubstituted" means that none of the hydrogen atoms have been replaced.

The term "aromatic radical" encompasses "aryl" and "heteroaryl".

The term "aryl" is preferably understood to mean a monovalent, aromatic or partly aromatic, mono- or bi- or tricyclic hydrocarbon ring having 6, 7, 8, 9, 10, 11, 12, 13 or 14 carbon atoms (a "C6-C14-aryl" group), especially a ring having 6 carbon atoms (a "C6-aryl" group), for example a phenyl group; or a ring having 9 carbon atoms (a "C9-aryl" group), for an indanyl or indenyl group, or a ring having 10 carbon atoms (a "Clo-aryl" group), for example a tetralinyl, dihydronaphthyl or naphthyl group, or a biphenyl group (a "C12-aryl" group) or a ring having 13 carbon atoms (a "C13-aryl" group), for a fluorenyl group, or a ring having 14 carbon atoms (a "C14-aryl" group), for example an anthracenyl group. The aryl group is preferably a phenyl group.

The term "heteroaryl" is preferably understood to mean a monovalent, monocyclic, bicyclic or tricyclic aromatic ring system having 5, 6, 7, 8, 9, 10, 11, 12, 13 or 14 ring atoms (5- to 14-membered heteroaryl group), especially having 5 or 6 or 9 or 10 atoms, and which at least one heteroatom, which may be identical or different, where the heteroatom is as oxygen, nitrogen or sulfur, and may additionally be benzofused in each case. More particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc. and benzo derivatives thereof, for example benzofuranyl, benzothienyl, benzoxazolyl, benzisoxazolyl, benzimidazolyl, benzotriazolyl, indazolyl, indolyl, isoindolyl etc.; or pyridinyl, pyridazinyl, pyrimidinyl, pyrazinyl, triazinyl etc. and benzo derivatives thereof, for example quinolinyl, quinazolinyl, isoquinolinyl etc.; or azocinyl, indolizinyl, purinyl etc. and benzo derivatives thereof, or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl or oxepinyl etc.

"Hydrolases" are enzymes that hydrolytically cleave esters, ethers, peptides, glycosides, acid anhydrides or C—C bonds in a reversible reaction. The term is used in the meaning customary to the person skilled in the art. Examples of hydrolases are listed further down. The term "hydrolase" encompasses "lipases", "esterases", "amidases" and "proteases".

"Lipases", "esterases", "amidases" and "proteases" are a subgroup belonging to the hydrolases. The term is used in the meaning customary to the person skilled in the art. Examples of lipases are listed further down.

In the novel process of the invention, rather than the discussed complex SMB separation of the racemic mixture of the amides (I)

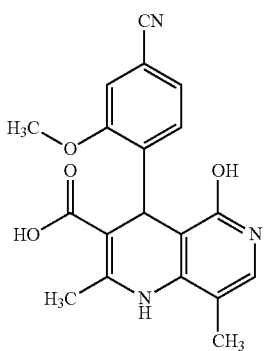

(I)

into the antipodes of the formula (Ia) and (Ib), an advantageous enzymatic optical resolution on a synthesis precursor, the racemic unit (II)

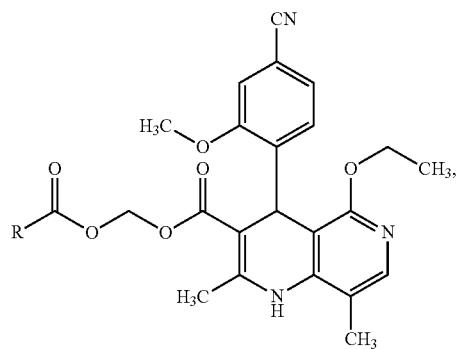

(II)

is undertaken.

The reaction of racemic dihydropyridine esters with hydrolases, preferably lipases, for optical resolution is described in the literature. Examples include: Torres et al., Org. Biomol. Chem., 2017, 15, 5171-5181; Xin et al., CN 2016-106279000; Verdecia et al., US 2014/0275042; Torres et al., Tetrahedron 71 (2015) 3976-3984; Sobolev et al., Biocatalysis and Biotransformations, 2004, 231-252 (Review); Schnell et al. J. Chem. Soc., Perkin Trans. 1-2000-4389.

The resolution of other substrates has additionally been described: Tetrahedron Letters, Volume 29, Issue 36, 1988, Pages 4623-4624; Biotechnology Letters, September 1994, Volume 16, Issue 9, pp 919-922.

Numerous attempts have been made to synthesize, with the aid of enzymatic methods, suitable chiral derivatives that can be used for synthesis of finerenone (Ia). The derivatives described here are notable for extremely poor solubility in water (<<100 mg/l) or in water-miscible organic solvents, and so it was very surprising to the person skilled in the art that it was possible to find conditions that permit preparation of chiral acyloxymethyl esters of (4S)-(4-cyano-2-methoxyphenyl)-5-ethoxy-2,8-dimethyl-1,4-dihydro-1,6-naphthyridine-3-carboxylic acid (IIa) in good yield and high enantiomeric purity.

A distinction has to be made between two cases for the enzymatic hydrolysis. Firstly that the target enantiomer having the 4S configuration (IIa) is hydrolysed and converted to the acid (IIIa), which is then separated off, or secondly that the enantiomer having the 4R configuration (IIb) is hydrolysed and the 4S-configured ester (IIa) remains in the solution and then is converted later to the acid (IIIa) after being separated off.

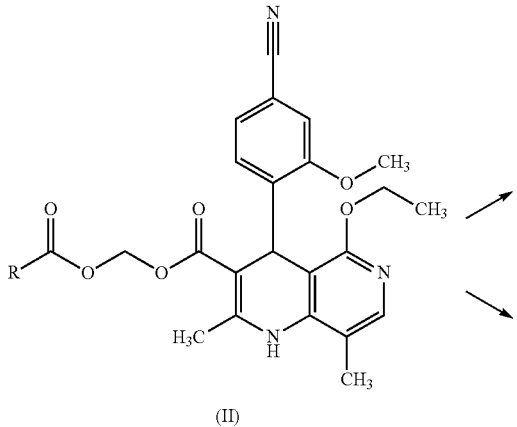

(II)

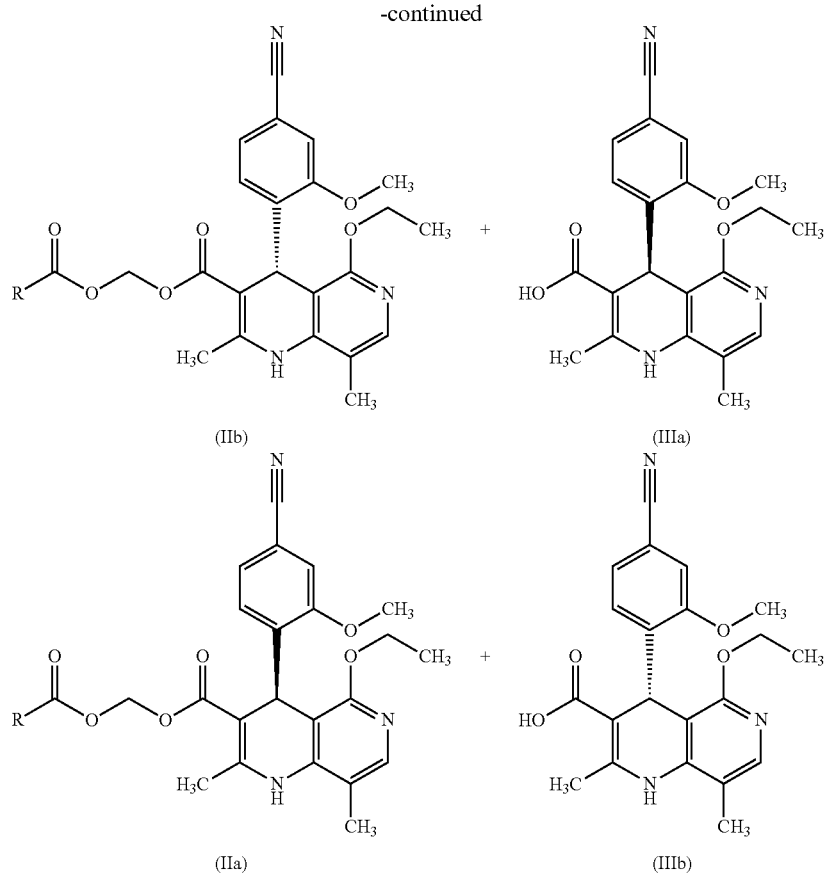

(IIb)  (IIIa)

(IIa)  (IIIb)

Both products, ester and acid, can be separated very easily from one another via extraction.

The conversion can be conducted using the following commercial enzymes:
- AK lipase from *Pseudomonas fluorescens* [CAS number 9001-62-1; preferably UniProtKB entry—Q7WZT7 (Sigma-Aldrich, Amano Enzyme)]
- type VII lipase from *Candida rugosa* (Sigma-Aldrich, L1754)
- lipase from *Candida rugosa* (Sigma-Aldrich 62316)
- Amano lipase M, from *Mucor javanicus* (Sigma-Aldrich 534803)
- Amano lipase PS. from *Burkholderia cepacia* (Sigma-Aldrich 534641)
- Amano lipase PS-IM (Sigma-Aldrich 709603)
- lipase from *Aspergillus niger* (Sigma-Aldrich 62301)
- lipase from *Thermomyces lanuginosus* (Sigma-Aldrich L0777)
- lipase from *Rhizomucor miehei* (Sigma-Aldrich L4277)
- lipase from *Candida antarctica* B (Lipozyme, Novozymes)
- lipase from *Candida antarctica* A (Novocor AD L, Novozymes)
- lipase from *Aspergillus oryzae* (Resinase HT, Novozymes)
- lipase from *Humicola insolens* (Novozym 51032, Novozymes)
- lipase from *Candida antarctica* B, immobilized (Novozym 435, Novozymes)
- lipase from *Thermomyces lanuginosus*, immobilized (Lipozyme TL IM, Novozymes)
- lipase from *Rhizomucor miehei*, immobilized (Novozym 40086, Novozymes)
- lipase from *Candida antarctica* in acrylic resin (Sigma-Aldrich L4777)
- lipase from porcine liver (Sigma-Aldrich E3019)

The conversion is effected in a monophasic or biphasic system with an aqueous buffer, for example sodium phosphate, potassium phosphate, preferably potassium phosphate, and a water-miscible or -immiscible organic solvent, for example ethanol, methanol, n-butanol, isopropanol, acetone, THF, DMF, DMSO, tert-butyl methyl ether, cyclopentyl methyl ether, 1,4-dioxane, 2-methyl-THF, toluene or mixtures thereof. The conversion is effected at a pH of pH 7.0 to pH 10, preferably between pH 7-8, more preferably pH 7. The pH can be kept constant by means of sufficient buffer capacity, or else by gradual dropwise addition of an inorganic base, for example KOH or NaOH, both as an aqueous solution. In some cases, it has been found to be advantageous to add additives, for example sugars, glycerol, Mg salts, Ca salts.

The conversion is effected at temperatures of 22-45° C., preferably 25-38° C.; the mixture is stirred for 10 hours to 10 days (depending on the enzyme used).

The following solvent combinations have been found to be particularly useful:
- 2-methyl-THF/potassium phosphate buffer pH 7
- 10% DMSO/90% 50 mM potassium phosphate buffer pH 7
- 20% tert-butyl methyl ether/80% 50 mM potassium phosphate buffer pH 7 water-saturated tert-butyl methyl ether/various buffers pH 7-pH 7.5

50% cyclopentyl methyl ether/50% 50 mM K phosphate buffer pH 7

1:1 w/w Triton X-100, 1.5% DMF/98.5% 50 mM potassium phosphate buffer pH 7-pH 8 water-saturated 1,4-dioxane/various buffers pH 7-pH 7.5

For workup of the reaction solution, the reaction can be stopped by adding saturated sodium chloride solution (or another salt solution, for example CaCl$_2$)) and then the product can be extracted by extraction with a suitable solvent. The product can be purified further by chromatography. In many cases, the crude product can also be recrystallized directly. It has generally been found to be advantageous to recrystallize the products (that generally show ee % values of >70%) once again in order thus to obtain ee % values of >99%. Useful solvents for the final recrystallization have been found to be mixtures of tert-butyl methyl ether with alcohols, for example ethanol, methanol, isopropanol or ethyl acetate or isopropyl acetate.

The invention further relates to a process for preparing (4S)-4-(4-cyano-2-methoxyphenyl)-5-ethoxy-2,8-dimethyl-1,4-dihydro-1,6-naphthyridine-3-carboxamide of the formula (Ia)

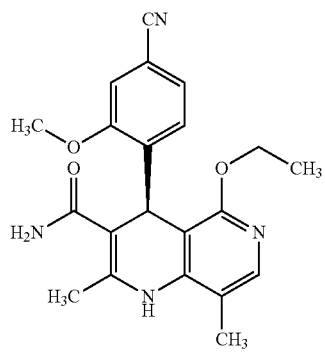

(Ia)

wherein the racemic acid of the formula (III)

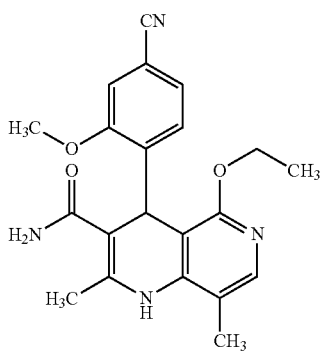

(III)

is reacted with halo esters of the general formula (V)

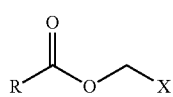

(V)

where

R is a linear or branched C1-C25 chain optionally substituted by an aromatic radical, X is chlorine or bromine, to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

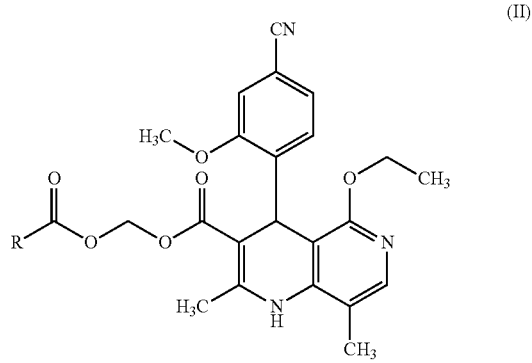

(II)

where R is a linear or branched C1-C25 chain optionally substituted by an aromatic radical, and this is converted by optical resolution using a hydrolase to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

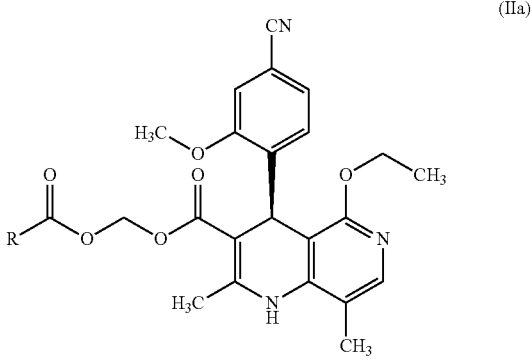

(IIa)

where R is a linear or branched C1-C25 chain optionally substituted by an aromatic radical, and this is hydrolysed in a THF/water mixture (2:1) with sodium hydroxide solution to give the compound of the formula (IIIa)

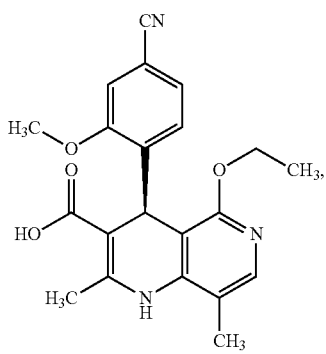

(IIIa)

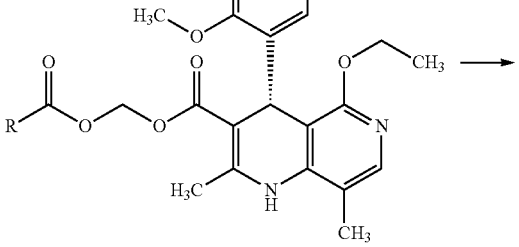

(IIb)

and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

The further conversion of the chiral acyloxymethyl ester (IIa) to finerenone (Ia) is described hereinafter.

Proceeding from the chiral acyloxymethyl esters (IIa or IIb), the acid (IIIa or IIIb) is obtained by alkaline hydrolysis and subsequent acidic workup:

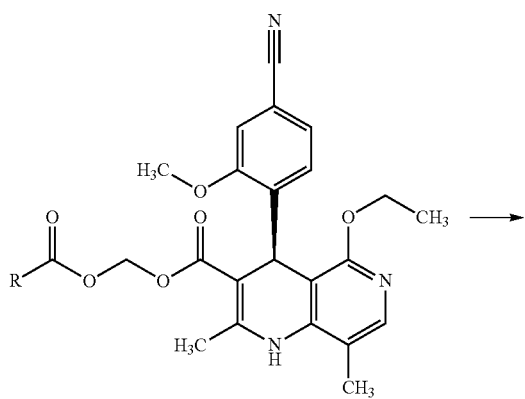

(IIa)

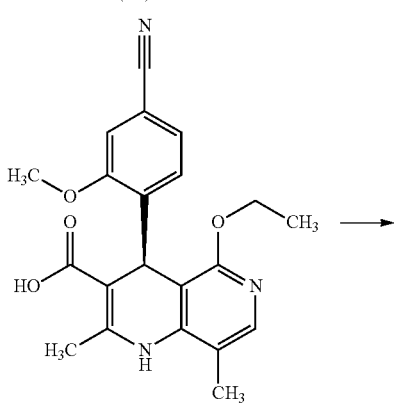

(IIIa)

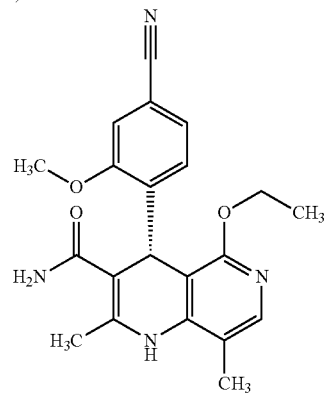

(IIIb)

The hydrolysis can be conducted in a manner known per se by the methods known to the person skilled in the art in organic solvents or with water-miscible solvents with the aid of an inorganic base. It has been found that the reaction can be run very easily in relatively concentrated form in mixtures of THF/water. For this purpose, preference is given to working in a mixture of THF/water 2:1 (9 times the amount), metering in the aqueous sodium hydroxide solution at 0-5° C., then stirring the mixture at 0-5° C. for 1-2 hours. It is also possible to use potassium hydroxide solution, but preference is given to using sodium hydroxide or potassium hydroxide. Workup is effected by extracting with MTBE (methyl tert-butyl ether) and ethyl acetate or else toluene only, and isolation by adjusting the pH to 7 with a mineral acid such as hydrochloric acid, sulfuric acid or phosphoric acid, but preferably hydrochloric acid. It is then possible to add saturated ammonium salt solution of the corresponding acid, but preferably ammonium chloride solution, with quantitative crystallization of the product. After isolation, the product is washed with water and with ethyl acetate or acetonitrile or acetone, but preferably acetonitrile, and dried under vacuum at 40-50° C. The yield is virtually quantitative (99%).

The subsequent conversion of the acid (IIIa or IIIb) to the amide (Ia or Ib) is described as follows: It has been found that, in a conversion of the acid (IIIa or IIIb) in THF, the amide (La or Ib) crystallizes directly out of the solution and can be obtained in high yield and purity. For this purpose, the carboxylic acid (IIIa or IIIb) is reacted with 1.1 to 1.6 equivalents, preferably 1.3-1.4 equivalents, of 1,1'-carbodiimidazole under DMAP catalysis (5-15 mol %, preferably 10 mol %/in some cases it has been found that the reaction can also be conducted without addition of DMAP) in THF to give the imidazolide, which takes place at temperatures between 20-50° C., the preferred approach having proven to be initially starting at 20° C., then stirring for 1 to 2 hours at this temperature and then further stirring at 50° C. for 2 to 3 hours. After the activation has ended, 3-8 equivalents, preferably 4.5 equivalents, of hexamethyldisilazane are added and the mixture is boiled for 16-24 hours, but preferably for 16 hours, under reflux. The disilylamide compound formed here can optionally be isolated, but it has been found to be more advantageous to continue in a one-pot reaction. After the reaction has ended, the mixture is therefore cooled to 0-3° C. and a mixture of water/or in a mixture with THF is added; it has been found to be advantageous to use 0.5 to 0.7 times the amount of water (based on reactant), particularly advantageous to use 0.52 times the amount of water. The water can be added directly or as a mixture with about one to two volume equivalents of THF. After quenching has ended, the mixture is heated to reflux for a total of 1-3 hours, preferably 1 hour. The mixture is cooled to 0° C. and stirred for 1-5 hours, preferably 3 hours, at this temperature, then the product is isolated by filtration or centrifugation. The product is washed with THF and water and dried under vacuum at elevated temperature (30 to 100° C., preferably at 40° C. to 70° C.). The yields are very high and are generally >93% of theory. The purity is generally >99% (HPLC, 100% method). The compound (Ia) can also be obtained directly by reacting with ammonia gas in an autoclave (about 25 to 30 bar). For this purpose, the preactivation described above is carried out and the reaction mixture is then heated under pressure under gaseous ammonia. On completion of the reaction, it is cooled and the product filtered off. The yields and purities thus achieved are comparable.

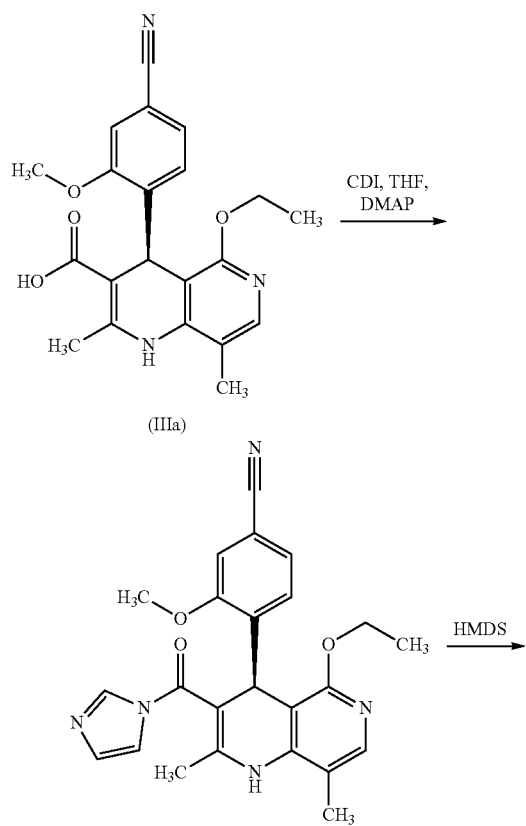

(IIIa)

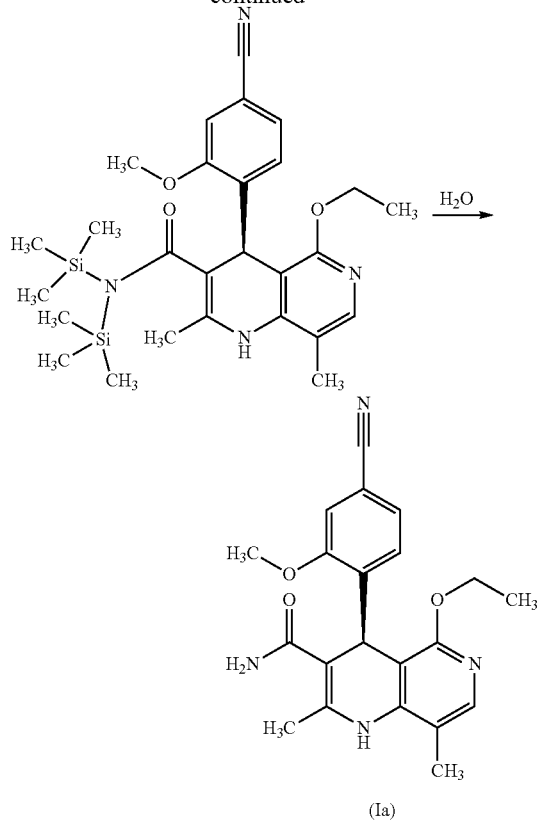

(Ia)

Final crystallization method (establishment of the final modification Mod A): For this purpose, (Ia), for GMP-related reasons, is first dissolved in ethanol and subjected to a particle filtration, and then the solvent is distilled off, either under reduced pressure or at standard temperature, preference being given to using toluene-denatured ethanol. The mixture is concentrated to about ⅓ to ⅕ of the volume; the product crystallizes out. This is cooled to 0° C. and the crystals then isolated and dried at 40-50° C. under vacuum. The yields are generally >90% of theory. The chemical purity achieved is >99.8% and the content ~100% correspond to the criteria for commercial products according to ICH guidelines. Residual solvent, in the case of ethanol, is <0.02%. The optical purity is >>99% e.e.

The noninventive process described here features several advantages over the prior art. No specific equipment (for example SMB, chiral chromatography methods) is required for separation of the enantiomers at the precursors of the finerenone synthesis (Ia). The enzymatic resolution can be conducted in entirely normal stirred reactors. The use of water as reaction medium saves costs with regard to costly solvents. The disposal of wastes is also found to be more environmentally friendly as a result than in former processes. The enzymatic optical resolution affords intermediate (IIa) generally with 70-91% enantiomeric excess (e.e. %). A relatively simple crystallization can increase enantiomeric excesses to >99% e.e., it being known that high-purity finerenone (Ia) can be obtained even with 93% e.e. material, since the incorrect enantiomer is lost in the downstream synthesis sequence as a result of crystallization. Therefore, ester (IIa) can be recrystallized in a relatively concentrated mode of operation, in order to keep the losses as low as possible.

There follows a description of further embodiments of the invention:

The present invention relates to a process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

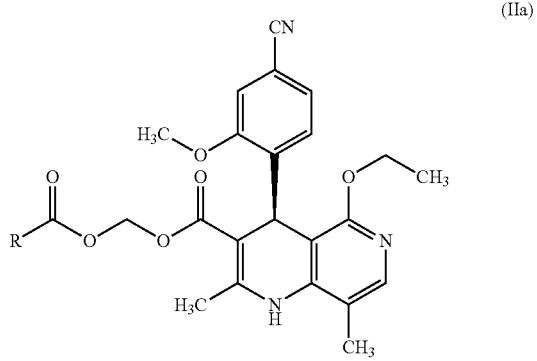

(IIa)

where R is a linear or branched C1-C25 chain optionally substituted by an aromatic radical, by optical resolution of (II)

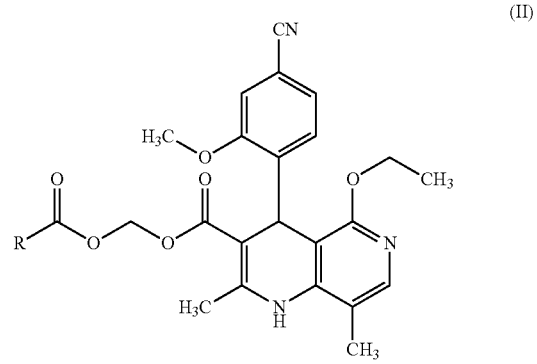

(II)

where R is a linear or branched C1-C25 chain optionally substituted by an aromatic radical, using a hydrolase.

Preference is given in the context of the present invention to a process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

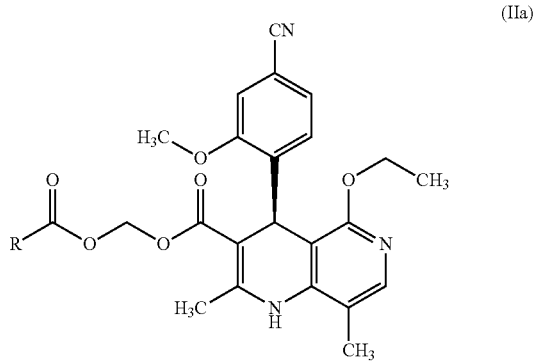

(IIa)

where R is a linear or branched C1-C25 chain optionally substituted by an aromatic radical, by optical resolution of (II)

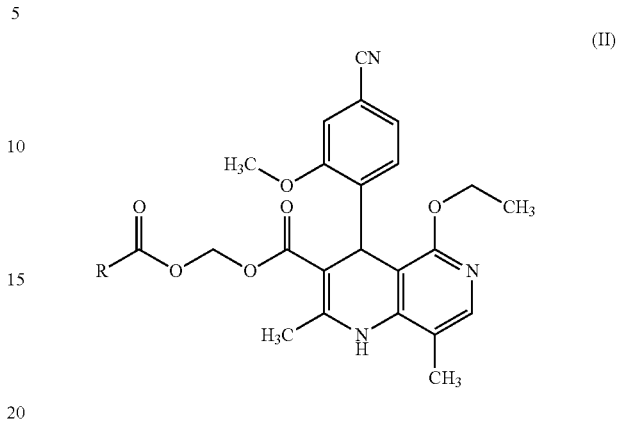

(II)

where R is a linear or branched C1-C25 chain optionally substituted by an aromatic radical, using a lipase.

Preference is given in the context of the present invention to a process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

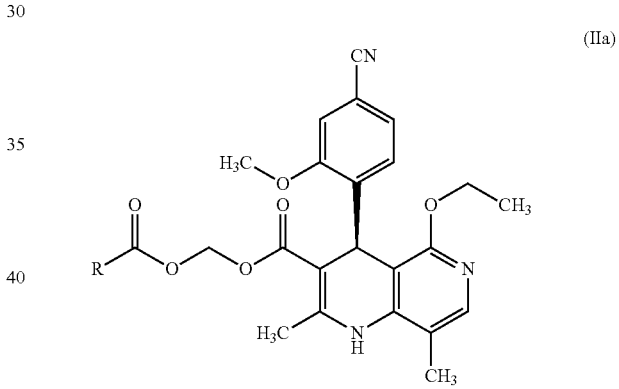

(IIa)

where R is a linear or branched C1-C25 chain optionally substituted by an aromatic radical, by optical resolution of (II)

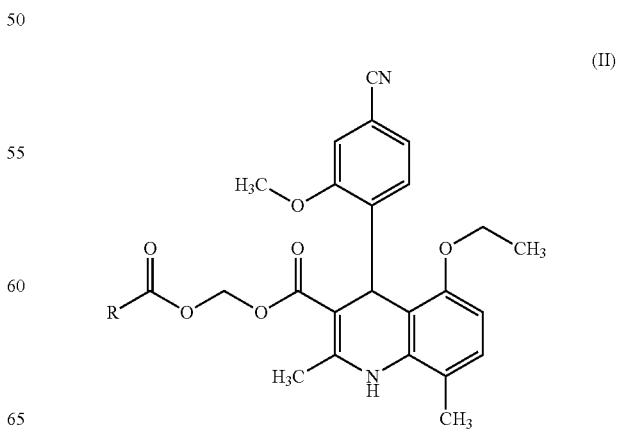

(II)

where R is a linear or branched C1-C25 chain optionally substituted by an aromatic radical, using AK lipase from *Pseudomonas fluorescens*.

Preference is given in the context of the present invention to a process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

where R is methyl, ethyl, n-propyl, isopropyl, tert-butyl, benzyl, n-butyl, n-pentyl or n-hexyl, by optical resolution of (II)

where R is methyl, ethyl, n-propyl, isopropyl, tert-butyl, benzyl, n-butyl, n-pentyl or n-hexyl, using a hydrolase.

Preference is given in the context of the present invention to a process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

where R is methyl, ethyl, n-propyl, isopropyl, tert-butyl, benzyl, n-butyl, n-pentyl or n-hexyl, by optical resolution of (II)

where R is methyl, ethyl, n-propyl, isopropyl, tert-butyl, benzyl, n-butyl, n-pentyl or n-hexyl, using a lipase.

Preference is given in the context of the present invention to a process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

where R is methyl, ethyl, n-propyl, isopropyl, tert-butyl, benzyl, n-butyl, n-pentyl or n-hexyl, by optical resolution of (II)

where R is methyl, ethyl, n-propyl, isopropyl, tert-butyl, benzyl, n-butyl, n-pentyl or n-hexyl, using AK lipase from *Pseudomonas fluorescens*.

Preference is given in the context of the present invention to a process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

where R is methyl, ethyl and isopropyl, n-butyl or n-pentyl, by optical resolution of (II)

where R is methyl, ethyl and isopropyl, n-butyl or n-pentyl, using a hydrolase.

Preference is given in the context of the present invention to a process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

where R is methyl, ethyl and isopropyl, n-butyl or n-pentyl, by optical resolution of (II)

where R is methyl, ethyl and isopropyl, n-butyl or n-pentyl, using a lipase.

Preference is given in the context of the present invention to a process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

where R is methyl, ethyl and isopropyl, n-butyl or n-pentyl, by optical resolution of (II)

where R is methyl, ethyl and isopropyl, n-butyl or n-pentyl, using AK lipase from *Pseudomonas fluorescens*.

Particular preference is given in the context of the present invention to a process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

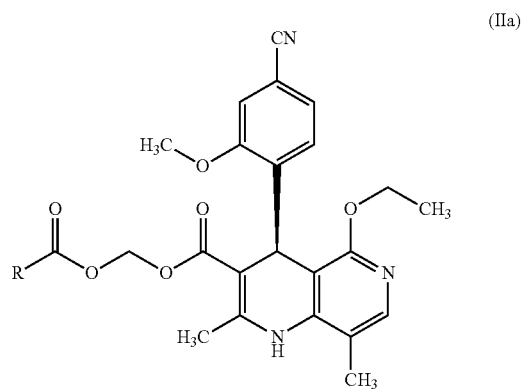

where R is methyl, by optical resolution of (II)

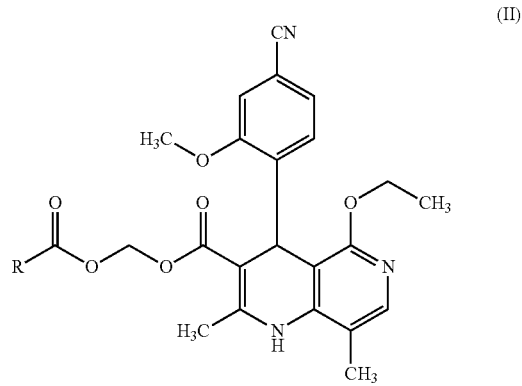

where R is methyl, using a hydrolase.

Particular preference is given in the context of the present invention to a process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

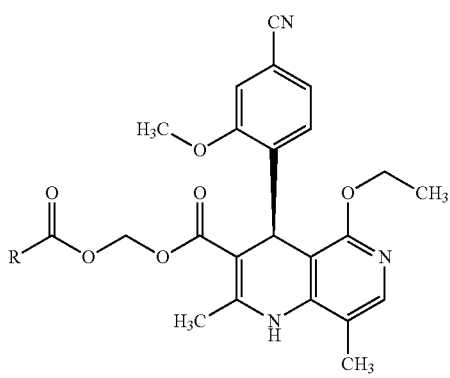

(IIa)

where R is methyl,
by optical resolution of (I)

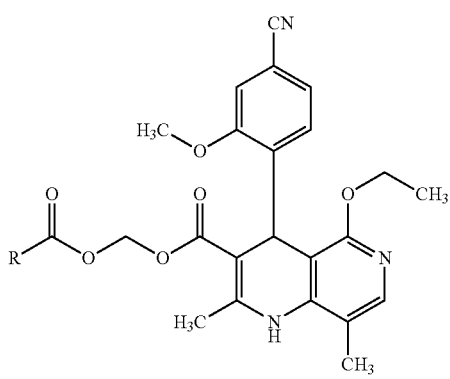

(II)

where R is methyl,
using a lipase.

Particular preference is given in the context of the present invention to a process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

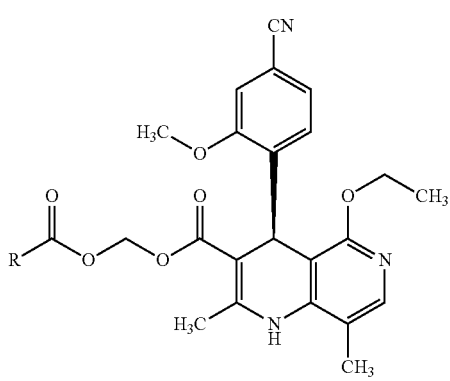

(IIa)

where R is methyl,
by optical resolution of (I)

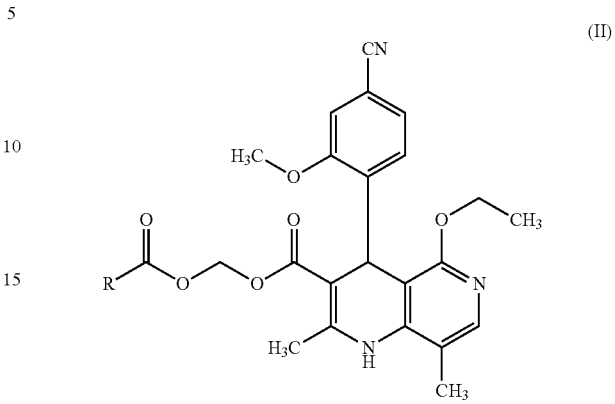

(II)

where R is methyl,
using AK lipase from *Pseudomonas fluorescens*.

The present invention also relates to a process for preparing (4S)-4-(4-cyano-2-methoxyphenyl)-5-ethoxy-2,8-dimethyl-1,4-dihydro-1,6-naphthyridine-3-carboxamide of the formula (Ia)

(Ia)

characterized in that the racemic acid of the formula (III)

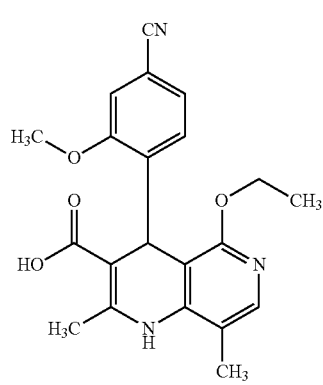

(III)

is reacted with halo esters of the general formula (V)

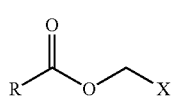
(V)

where
R is a linear or branched C1-C25 chain optionally substituted by an aromatic radical,
X is chlorine or bromine,
to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

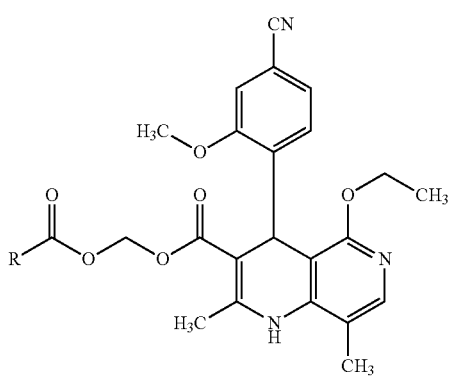
(II)

where R is a linear or branched C1-C25 chain optionally substituted by an aromatic radical,
and this is converted by optical resolution using
a hydrolase
to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

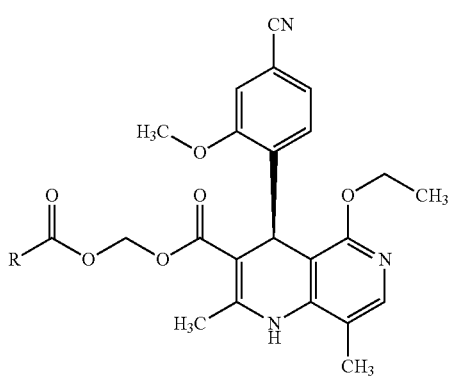
(IIa)

where R is a linear or branched C1-C25 chain optionally substituted by an aromatic radical,
and this is hydrolysed in a THF/water mixture (2:1) with sodium hydroxide solution to give the compound of the formula (IIIa)

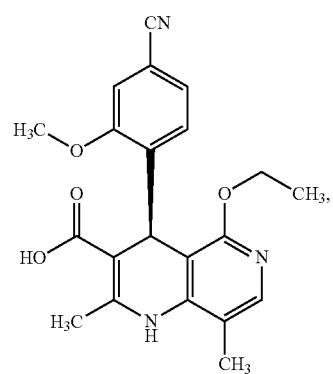
(IIIa)

(IIIa), and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia)

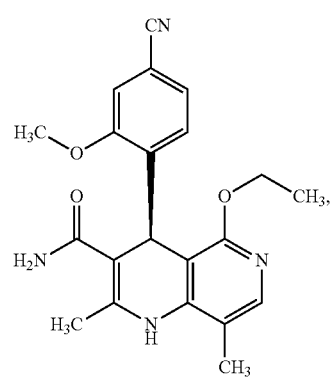
(Ia)

characterized in that the racemic acid of the formula (III)

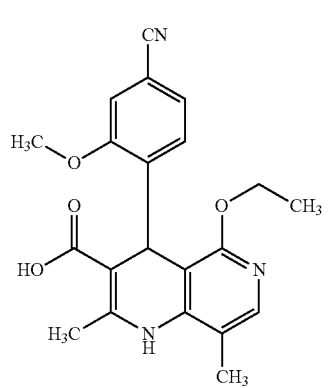
(III)

is reacted with halo esters of the general formula (V)

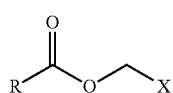
(V)

where
R is a linear or branched C1-C25 chain optionally substituted by an aromatic radical,
X is chlorine or bromine,
to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

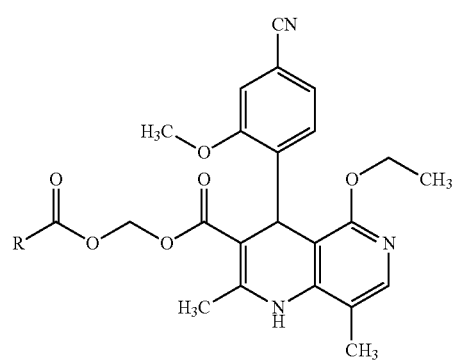
(II)

where R is a linear or branched C1-C25 chain optionally substituted by an aromatic radical,
and this is converted by optical resolution using
a lipase
to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

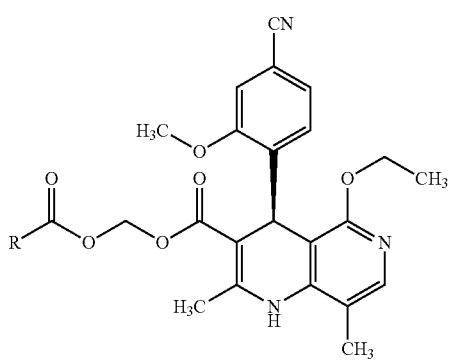
(IIa)

where R is a linear or branched C1-C25 chain optionally substituted by an aromatic radical,
and this is hydrolysed in a THF/water mixture (2:1) with sodium hydroxide solution to give the compound of the formula (IIIa)

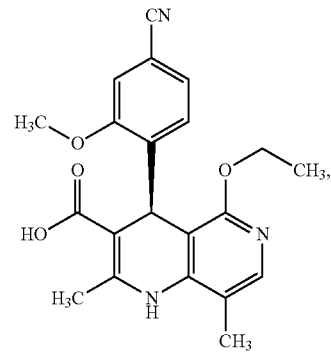
(IIIa)

and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia)

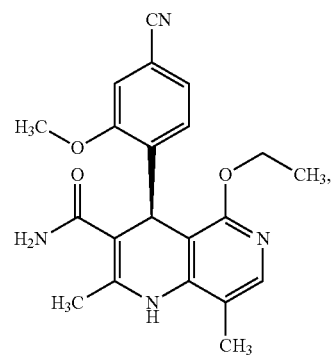
(Ia)

characterized in that the racemic acid of the formula (III)

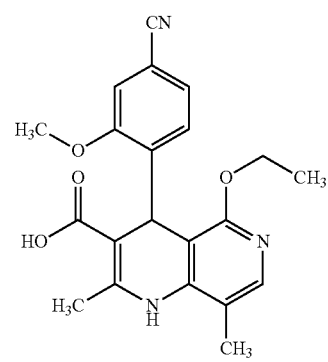
(III)

is reacted with halo esters of the general formula (V)

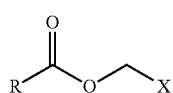

where

R is a linear or branched C1-C25 chain optionally substituted by an aromatic radical, X is chlorine or bromine, to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

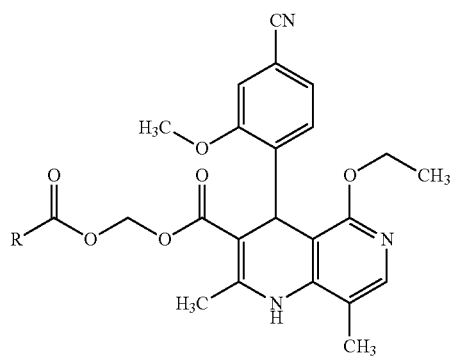

where R is a linear or branched C1-C25 chain optionally substituted by an aromatic radical, and this is converted by optical resolution using AK lipase from *Pseudomonas fluorescens* to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

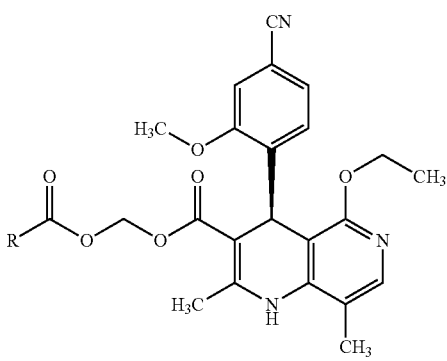

where R is a linear or branched C1-C25 chain optionally substituted by an aromatic radical, and this is hydrolysed in a THF/water mixture (2:1) with sodium hydroxide solution to give the compound of the formula (IIIa)

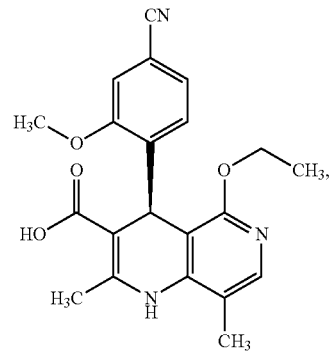

and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia), characterized in that the racemic acid of the formula (III)

is reacted with halo esters of the general formula (V)
where
R is methyl, ethyl, n-propyl, isopropyl, tert-butyl, benzyl, n-butyl, n-pentyl or n-hexyl,
X is chlorine or bromine,
to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)
where
R is methyl, ethyl, n-propyl, isopropyl, tert-butyl, benzyl, n-butyl, n-pentyl or n-hexyl,
and this is converted by optical resolution using
a hydrolase
to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)
where
R is methyl, ethyl, n-propyl, isopropyl, tert-butyl, benzyl, n-butyl, n-pentyl or n-hexyl, and this is hydrolysed in a THF/water mixture (2:1) with sodium hydroxide solution to give the compound of the formula (IIIa),
and this compound of the formula (IIia) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THE/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia),
characterized in that the racemic acid of the formula (III) is reacted with halo esters of the general formula (V)
where
R is methyl, ethyl, n-propyl, isopropyl, tert-butyl, benzyl, n-butyl, n-pentyl or n-hexyl,
X is chlorine or bromine, to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)
where
R is methyl, ethyl, n-propyl, isopropyl, tert-butyl, benzyl, n-butyl, n-pentyl or n-hexyl,
and this is converted by optical resolution using
a lipase
to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)
where
R is methyl, ethyl, n-propyl, isopropyl, tert-butyl, benzyl, n-butyl, n-pentyl or n-hexyl, and this is hydrolysed in a THE/water mixture (2:1) with sodium hydroxide solution to give the compound of the formula (IIIa),
and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia), characterized in that the racemic acid of the formula (III)
is reacted with halo esters of the general formula (V)
where
R is methyl, ethyl, n-propyl, isopropyl, tert-butyl, benzyl, n-butyl, n-pentyl or n-hexyl,
X is chlorine or bromine,
to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)
where
R is methyl, ethyl, n-propyl, isopropyl, tert-butyl, benzyl, n-butyl, n-pentyl or n-hexyl,
and this is converted by optical resolution using
AK lipase from *Pseudomonas fluorescens*
to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)
where
R is methyl, ethyl, n-propyl, isopropyl, tert-butyl, benzyl, n-butyl, n-pentyl or n-hexyl, and this is hydrolysed in a THF/water mixture (2:1) with sodium hydroxide solution to give the compound of the formula (IIIa), and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia), characterized in that the racemic acid of the formula (III)
is reacted with halo esters of the general formula (V)
where
R is methyl, ethyl and isopropyl, n-butyl or n-pentyl,
X is chlorine or bromine,
to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)
where
R is methyl, ethyl and isopropyl, n-butyl or n-pentyl,
and this is converted by optical resolution using
a hydrolase
to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)
where
R is methyl, ethyl and isopropyl, n-butyl or n-pentyl,
and this is hydrolysed in a THF/water mixture (2:1) with sodium hydroxide solution to give the compound of the formula (IIIa),
and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia),
characterized in that the racemic acid of the formula (III)
is reacted with halo esters of the general formula (V)
where
R is methyl, ethyl and isopropyl, n-butyl or n-pentyl,
X is bromine,
to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)
where
R is methyl, ethyl and isopropyl, n-butyl or n-pentyl,
and this is converted by optical resolution using
a hydrolase
to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)
where
R is methyl, ethyl and isopropyl, n-butyl or n-pentyl,
and this is hydrolysed in a THF/water mixture (2:1) with sodium hydroxide solution to give the compound of the formula (IIIa),
and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia),
characterized in that the racemic acid of the formula (III)
is reacted with halo esters of the general formula (V)
where
R is methyl, ethyl and isopropyl, n-butyl or n-pentyl,
X is chlorine or bromine, to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)
where R is methyl, ethyl and isopropyl, n-butyl or n-pentyl, and this is converted by optical resolution using a lipase to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

where

R is methyl, ethyl and isopropyl, n-butyl or n-pentyl, and this is hydrolysed in a THF/water mixture (2:1) with sodium hydroxide solution to give the compound of the formula (IIIa), and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia), characterized in that the racemic acid of the formula (III) is reacted with halo esters of the general formula (V)

where

R is methyl, ethyl and isopropyl, n-butyl or n-pentyl,

X is bromine, to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

where

R is methyl, ethyl and isopropyl, n-butyl or n-pentyl, and this is converted by optical resolution using a lipase to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

where

R is methyl, ethyl and isopropyl, n-butyl or n-pentyl, and this is hydrolysed in a THF/water mixture (2:1) with sodium hydroxide solution to give the compound of the formula (IIIa), and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia), characterized in that the racemic acid of the formula (III) is reacted with halo esters of the general formula (V)

where

R is methyl, ethyl and isopropyl, n-butyl or n-pentyl,

X is chlorine or bromine, to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

where

R is methyl, ethyl and isopropyl, n-butyl or n-pentyl, and this is converted by optical resolution using AK lipase from *Pseudomonas fluorescens* to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

where

R is methyl, ethyl and isopropyl, n-butyl or n-pentyl, and this is hydrolysed in a THE/water mixture (2:1) with sodium hydroxide solution to give the compound of the formula (IIIa), and this compound of the formula (IIIa) is then reacted in THE as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia), characterized in that the racemic acid of the formula (III)

is reacted with halo esters of the general formula (V)

where

R is methyl, ethyl and isopropyl, n-butyl or n-pentyl,

X is bromine, to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

where

R is methyl, ethyl and isopropyl, n-butyl or n-pentyl, and this is converted by optical resolution using AK lipase from *Pseudomonas fluorescens* to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

where

R is methyl, ethyl and isopropyl, n-butyl or n-pentyl, and this is hydrolysed in a THF/water mixture (2:1) with sodium hydroxide solution to give the compound of the formula (IIIa), and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia)

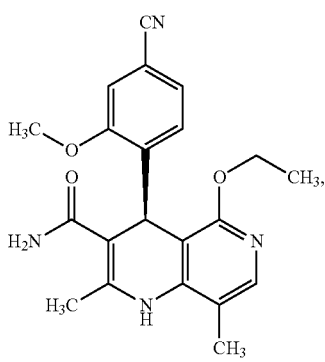

characterized in that the racemic acid of the formula (III)

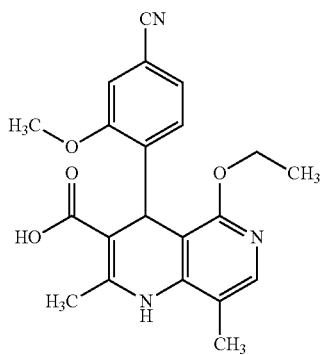

is reacted with halo esters of the general formula (V)

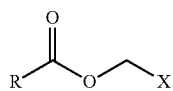

where
R is methyl,
X is chlorine or bromine,
to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

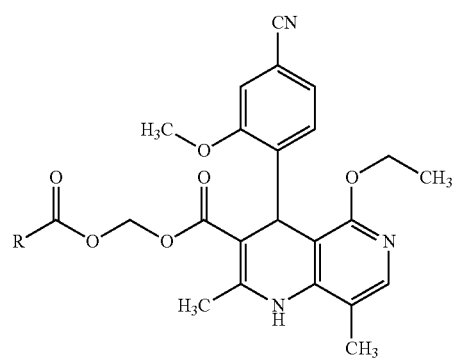

R is methyl,
and this is converted by optical resolution using a hydrolase
to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

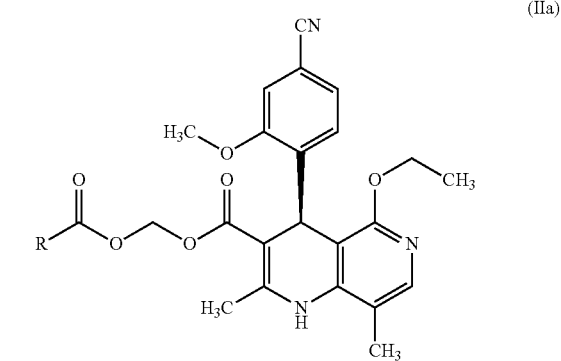

R is methyl,
and this is hydrolysed in a THF/water mixture (2:1) with sodium hydroxide solution to give the compound of the formula (IIIa)

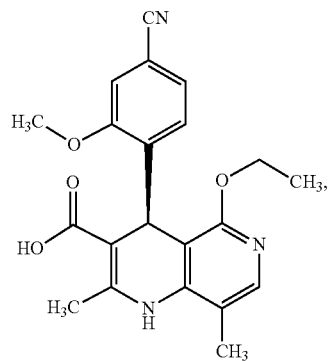

and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia)

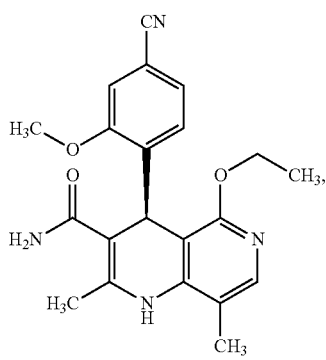

(Ia)

characterized in that the racemic acid of the formula (III)

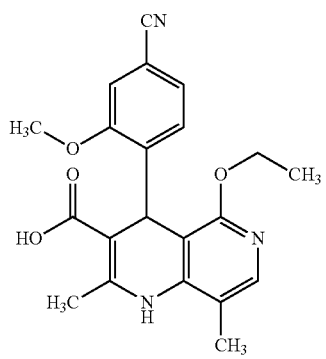

(III)

is reacted with halo esters of the general formula (V)

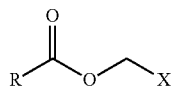

(V)

where

R is methyl,

X is bromine, to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

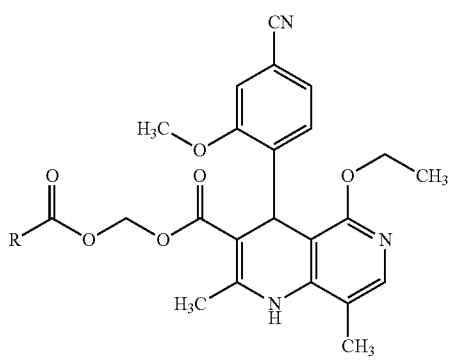

(II)

R is methyl, and this is converted by optical resolution using a hydrolase to the enantiomeric acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

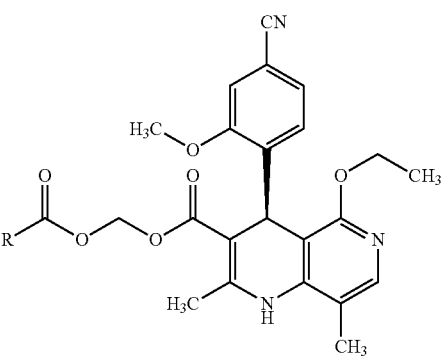

(IIa)

R is methyl, and this is hydrolysed in a THF/water mixture (2:1) with sodium hydroxide solution to give the compound of the formula (IIIa)

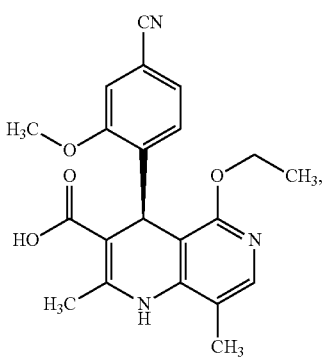

(IIIa)

and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia)

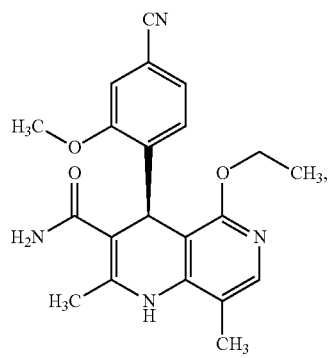

(Ia)

characterized in that the racemic acid of the formula (III)

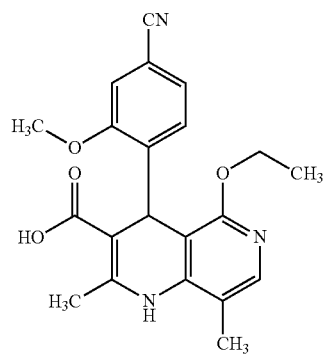

(III)

is reacted with halo esters of the general formula (V)

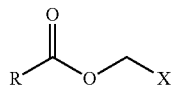

(V)

where
R is methyl,
X is chlorine or bromine,
to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

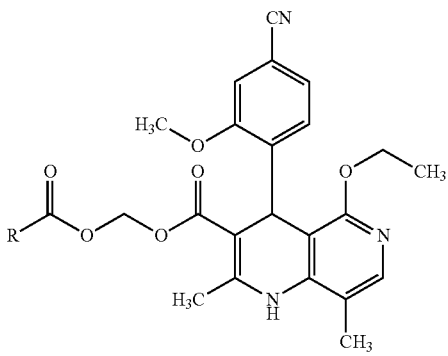

(II)

R is methyl,
and this is converted by optical resolution using
a lipase
to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

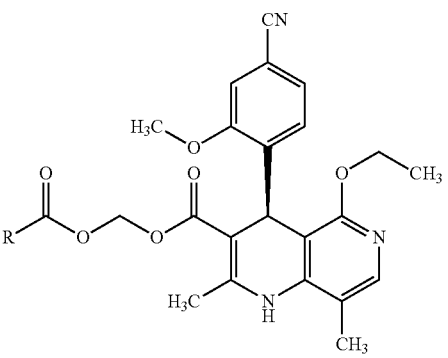

(IIa)

R is methyl,
and this is hydrolysed in a THF/water mixture (2:1) with sodium hydroxide solution to give the compound of the formula (IIIa)

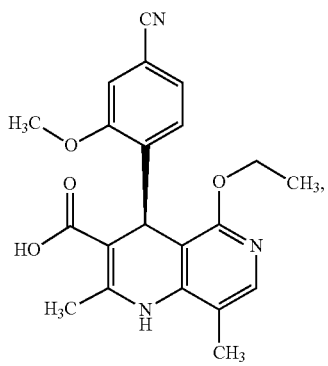

(IIIa)

and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia)

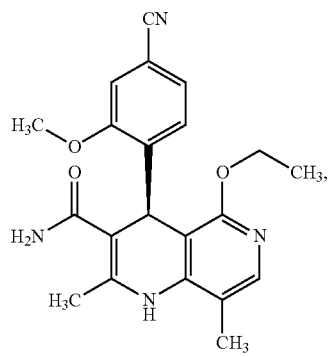

(Ia)

characterized in that the racemic acid of the formula (III)

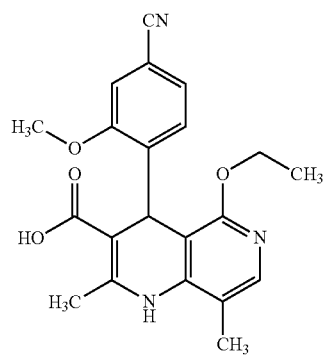

(III)

is reacted with halo esters of the general formula (V)

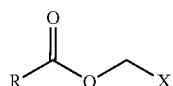

(V)

where

R is methyl,

X is bromine, to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

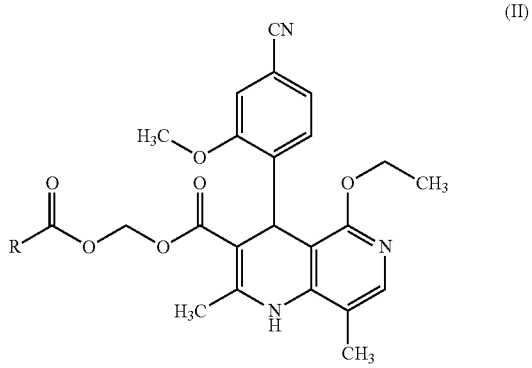

(II)

R is methyl, and this is converted by optical resolution using a lipase to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

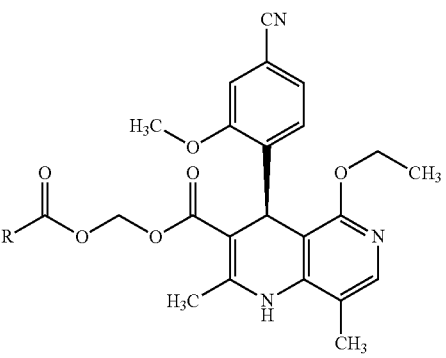

(IIa)

R is methyl, and this is hydrolysed in a THF/water mixture (2:1) with sodium hydroxide solution to give the compound of the formula (IIIa)

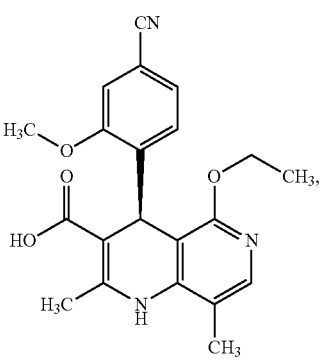

(IIIa)

and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia)

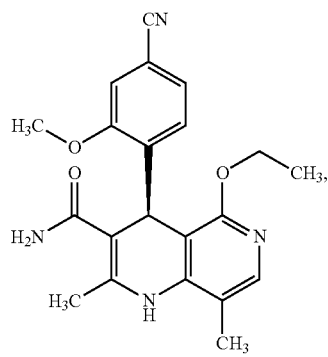
(Ia)

characterized in that the racemic acid of the formula (III)

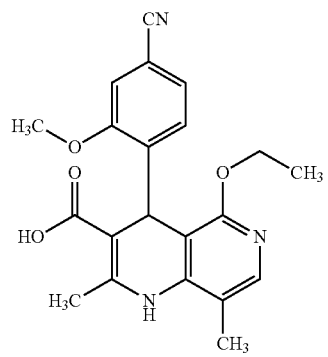
(III)

is reacted with halo esters of the general formula (V)

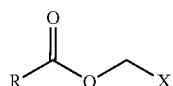
(V)

where
R is methyl,
X is chlorine or bromine,
to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

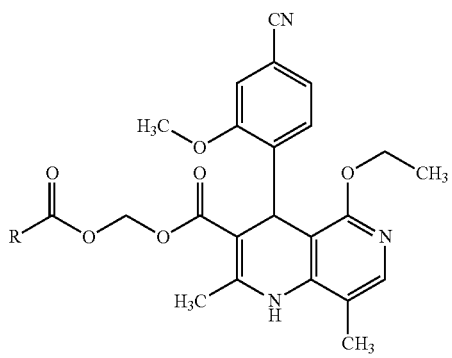
(II)

where
R is methyl,
and this is converted by optical resolution using
AK lipase from *Pseudomonas fluorescens*
to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

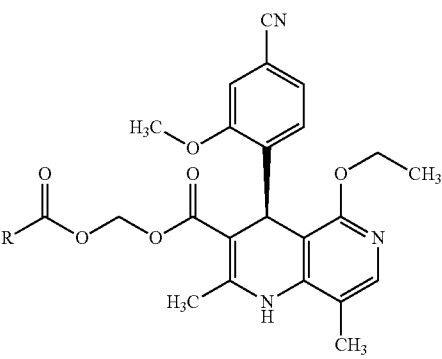
(IIa)

where
R is methyl,
and this is hydrolysed in a THF/water mixture (2:1) with sodium hydroxide solution to give the compound of the formula (IIIa)

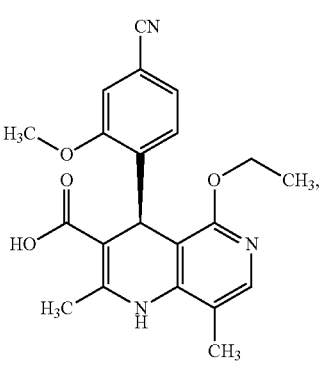
(IIIa)

and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia)

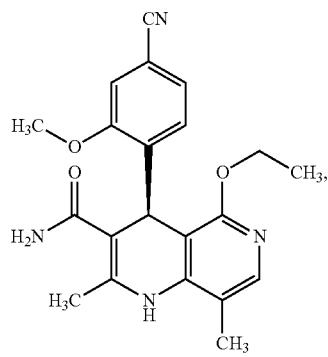

(Ia)

characterized in that the racemic acid of the formula (III)

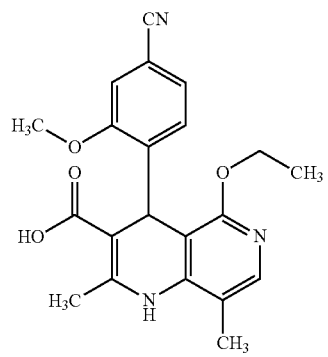

(III)

is reacted with halo esters of the general formula (V)

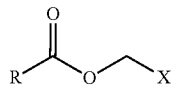

(V)

where
R is methyl,
X is bromine,
to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

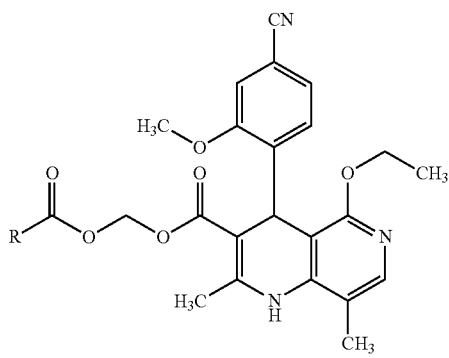

(II)

where
R is methyl,
and this is converted by optical resolution using
AK lipase from *Pseudomonas fluorescens*
to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

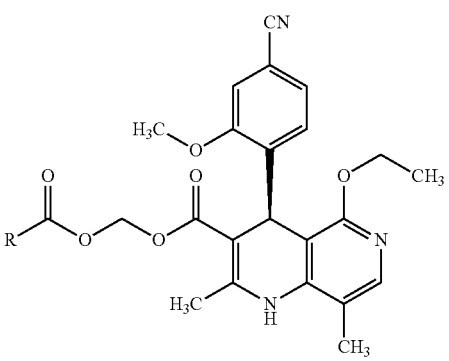

(IIa)

where
R is methyl,
and this is hydrolysed in a THF/water mixture (2:1) with sodium hydroxide solution to give the compound of the formula (IIIa)

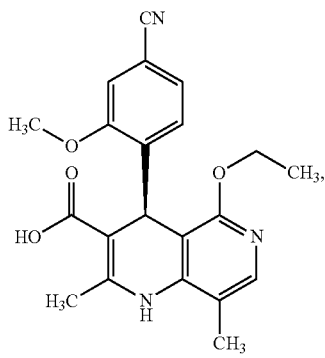

(IIIa)

and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia), characterized in that the racemic acid of the formula (III) is reacted with halo esters of the general formula (V) where R is methyl, ethyl and isopropyl, n-butyl or n-pentyl, X is chlorine, to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

where

R is methyl, ethyl and isopropyl, n-butyl or n-pentyl, and this is converted by optical resolution using a hydrolase to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

where

R is methyl, ethyl and isopropyl, n-butyl or n-pentyl, and this is hydrolysed in a THF/water mixture (2:1) with sodium hydroxide solution to give the compound of the formula (IIIa), and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia), characterized in that the racemic acid of the formula (III) is reacted with halo esters of the general formula (V) where R is methyl, ethyl and isopropyl, n-butyl or n-pentyl, X is chlorine, to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

where

R is methyl, ethyl and isopropyl, n-butyl or n-pentyl, and this is converted by optical resolution using a lipase to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

where

R is methyl, ethyl and isopropyl, n-butyl or n-pentyl, and this is hydrolysed in a THF/water mixture (2:1) with sodium hydroxide solution to give the compound of the formula (IIIa), and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia), characterized in that the racemic acid of the formula (III) is reacted with halo esters of the general formula (V) where R is methyl, ethyl and isopropyl, n-butyl or n-pentyl, X is chlorine, to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

where

R is methyl, ethyl and isopropyl, n-butyl or n-pentyl, and this is converted by optical resolution using AK lipase from *Pseudomonas fluorescens* to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

where

R is methyl, ethyl and isopropyl, n-butyl or n-pentyl, and this is hydrolysed in a THF/water mixture (2:1) with sodium hydroxide solution to give the compound of the formula (IIIa), and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia)

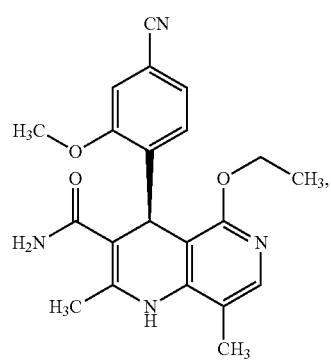

(Ia)

characterized in that the racemic acid of the formula (III)

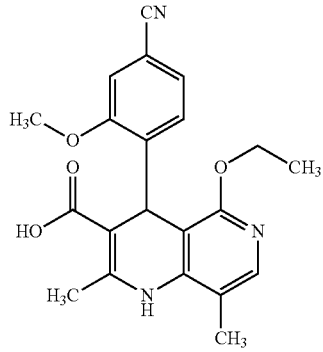 (III)

is reacted with halo esters of the general formula (V)

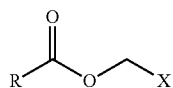 (V)

where

R is methyl,

X is chlorine, to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

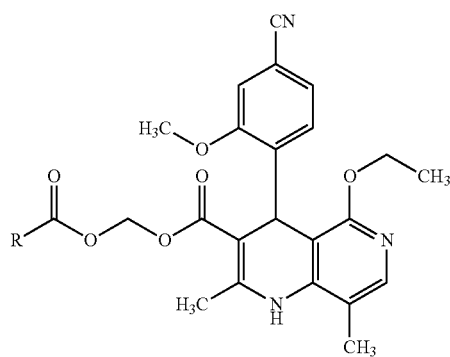 (II)

R is methyl, and this is converted by optical resolution using a lipase to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

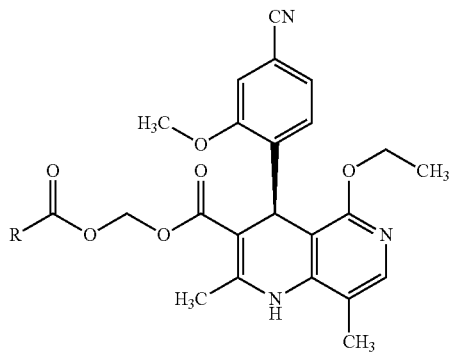 (IIa)

R is methyl, and this is hydrolysed in a THF/water mixture (2:1) with sodium hydroxide solution to give the compound of the formula (IIIa)

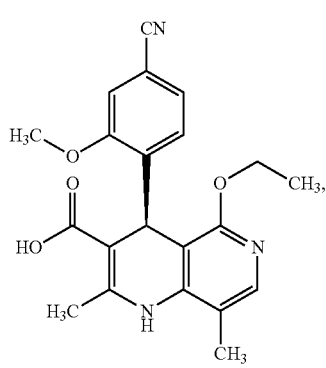 (IIIa)

and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

Preference is given in the context of the present invention to a process for preparing (4S)-4-(4-cyano-2-methoxyphenyl)-5-ethoxy-2,8-dimethyl-1,4-dihydro-1,6-naphthyridine-3-carboxamide of the formula (Ia)

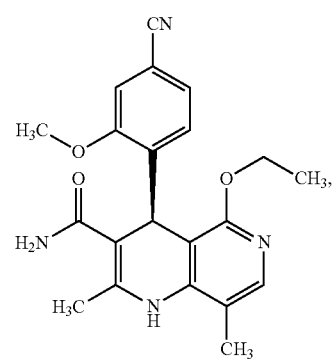 (Ia)

characterized in that the racemic acid of the formula (III)

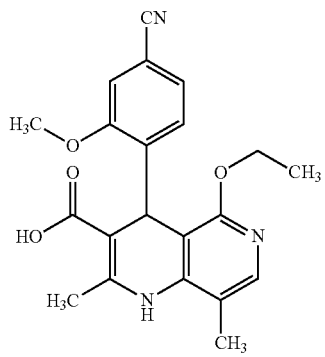
(III)

is reacted with halo esters of the general formula (V)

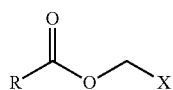
(V)

where
R is methyl,
X is chlorine,
to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

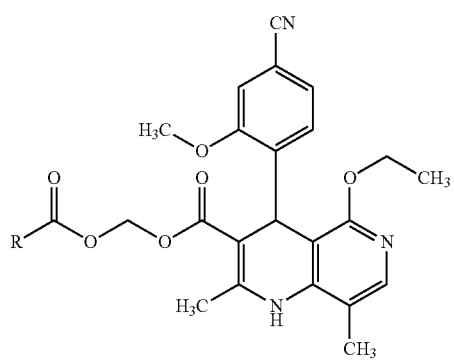
(II)

where
R is methyl,
and this is converted by optical resolution using
AK lipase from *Pseudomonas fluorescens*
to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

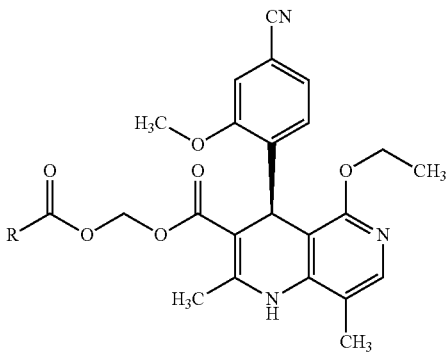
(IIa)

where
R is methyl,
and this is hydrolysed in a THF/water mixture (2:1) with sodium hydroxide solution to give the compound of the formula (IIIa)

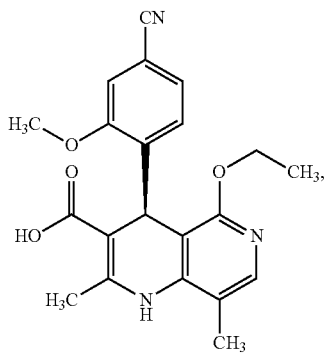
(IIIa)

and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

The conversion is effected in organic solvents such as dimethylformamide, dimethylacetamide, NMP, acetonitrile, THF, DMSO, sulfolane, acetone, 2-butanone, in the presence of an organic or inorganic base, for example triethylamine, tributylamine, pyridine, potassium carbonate, caesium carbonate, sodium carbonate, potassium hydrogencarbonate, sodium hydrogencarbonate, lithium hydroxide. The conversion is effected at 0° C. to 80° C., preferably at 20-60° C., more preferably at 20-40° C. The crude products obtained after workup are purified by crystallization.

The preparation of the acid (III) is described in WO 2016/016287 A1 (example 6).

The preparation of the halo esters (V) is conducted analogously to the synthesis described in G. Sosnovsky, N. U. M. Rao, S. W. Li, H. M. Swartz, J. Org. Chem. 1988, 54, 3667 and N. P. Mustafaev, M. A. Kulieva, K. N. Mustafaev, T. N. Kulibekova, G. A. Kakhramanova, M. R. Safarova, N. N. Novotorzhina, Russ. J. Org. Chem. 2012, 49, 198.

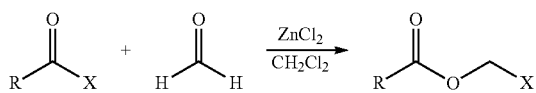

The invention additionally also relates to the use of a hydrolase in a process for preparing a compound of formula (IIa).

In one embodiment, the invention relates to the use of a hydrolase in a process for preparing a compound of formula (IIa) by optical resolution of the compound (II).

In a further embodiment, the invention relates to the use of a hydrolase in a process for preparing a compound of formula (IIa) by optical resolution of the compound (II), wherein the process corresponds to one of the embodiments of the process for preparing a compound of formula (IIa) as elucidated further up.

The invention also relates to the use of a hydrolase in a process for preparing a compound of formula (Ia).

In one embodiment, the invention relates to the use of a hydrolase for preparation of a compound of formula (Ia), wherein the process corresponds to one of the embodiments of the process for preparing a compound of formula (Ia) as elucidated further up.

The following paragraphs 1. to 10. constitute further embodiments of the invention:

1. Process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

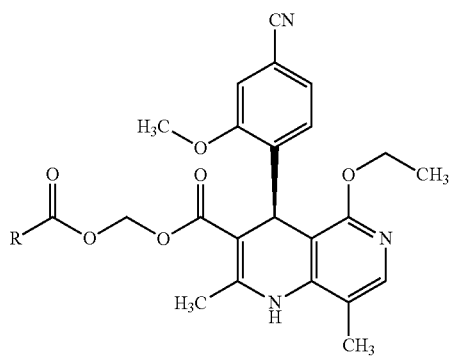

where R is a linear or branched C1-C25 chain optionally substituted by an aromatic radical, by optical resolution of (II)

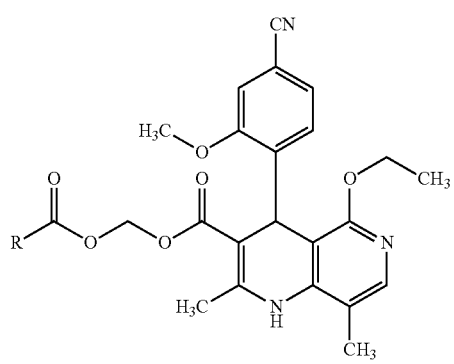

where R is a linear or branched C1-C25 chain optionally substituted by an aromatic radical, using a hydrolase.

2. Process according to paragraph 1, characterized in that R is methyl, ethyl, n-propyl, isopropyl, tert-butyl, benzyl, n-butyl, n-pentyl or n-hexyl.

3. Process according to paragraph 1 or 2, characterized in that

R is methyl.

4. Process according to paragraph 1, 2 or 3, characterized in that the hydrolase used is a lipase.

5. Process according to paragraph 4, characterized in that AK lipase from *Pseudomonas fluorescens* is used.

6. Process for preparing (4S)-4-(4-cyano-2-methoxyphenyl)-5-ethoxy-2,8-dimethyl-1,4-dihydro-1,6-naphthyridine-3-carboxamide of the formula (La)

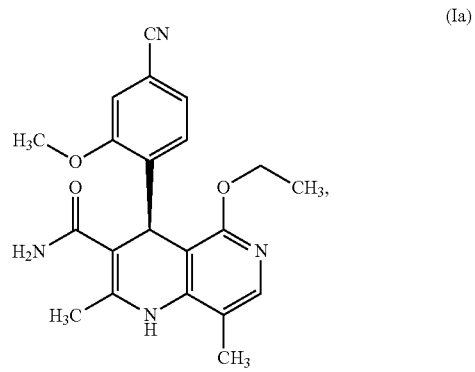 [SMILES: CCOc1ncc(C)c2c1[C@H](c1ccc(C#N)cc1OC)C(C(N)=O)=C(C)N2]

characterized in that the racemic acid of the formula (III)

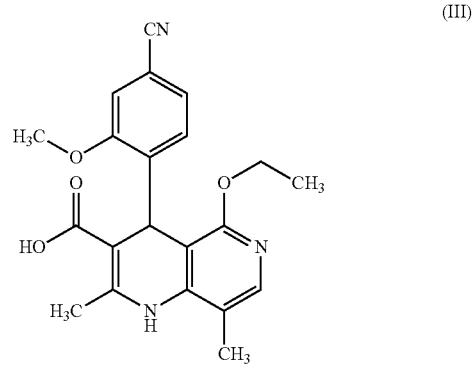 [SMILES: CCOc1ncc(C)c2c1C(c1ccc(C#N)cc1OC)C(C(=O)O)=C(C)N2]

is reacted with halo esters of the general formula (V)

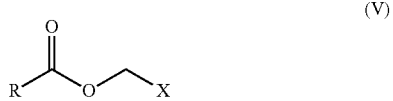

where
R is a linear or branched C1-C25 chain optionally substituted by an aromatic radical,
X is chlorine or bromine,
to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

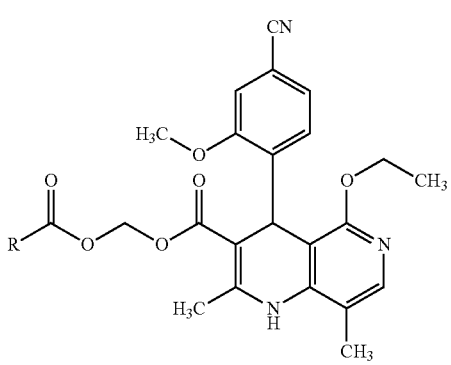

where R is a linear or branched C1-C25 chain optionally substituted by an aromatic radical,
and this is converted by optical resolution using
a hydrolase
to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

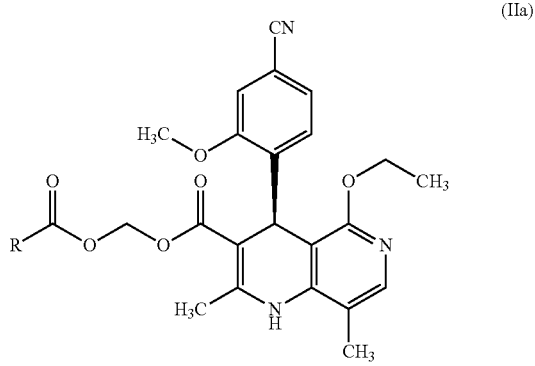

where R is a linear or branched C1-C25 chain optionally substituted by an aromatic radical,
and this is hydrolysed in a THF/water mixture (2:1) with sodium hydroxide solution to give the compound of the formula (IIIa)

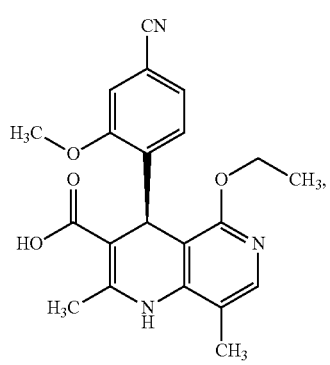

and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

7. Process according to paragraph 6, characterized in that
R is methyl, ethyl, n-propyl, isopropyl, tert-butyl, benzyl, n-butyl, n-pentyl or n-hexyl,
and
X is bromine.

8. Process according to paragraph 6 or 7, characterized in that
R is methyl,
and
X is bromine.

9. Process according to paragraph 6, 7 or 8, characterized in that lipase is used for the optical resolution.

10. Process according to paragraph 9, characterized in that AK lipase from *Pseudomonas fluorescens* is used for the optical resolution.

Paragraphs 1. to 10.

The following paragraphs 1. to 10. constitute further embodiments of the invention:

1. Process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

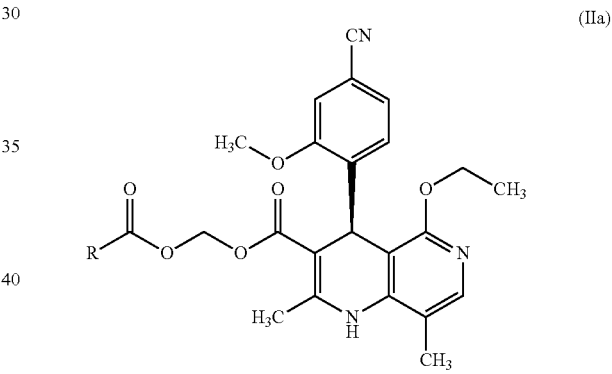

where R is a linear or branched C1-C25 chain optionally substituted by an aromatic radical, by optical resolution of (II)

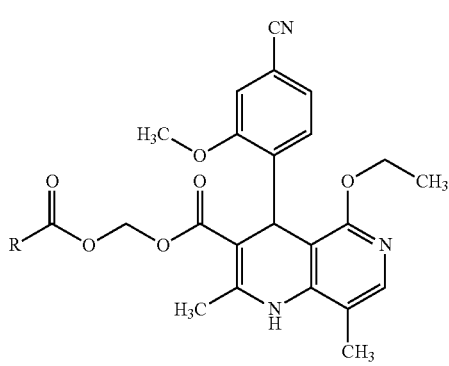

where R is a linear or branched C1-C25 chain optionally substituted by an aromatic radical, using a hydrolase.

2. Process according to paragraph 1, characterized in that
R is methyl, ethyl, n-propyl, isopropyl, tert-butyl, benzyl, n-butyl, n-pentyl or n-hexyl.

3. Process according to paragraph 1 or 2, characterized in that
R is methyl.

4. Process according to paragraph 1, 2 or 3, characterized in that the hydrolase used is a lipase.

5. Process according to paragraph 4, characterized in that AK lipase from *Pseudomonas fluorescens* is used.

6. Process for preparing (4S)-4-(4-cyano-2-methoxyphenyl)-5-ethoxy-2,8-dimethyl-1,4-dihydro-1,6-naphthyridine-3-carboxamide of the formula (Ia)

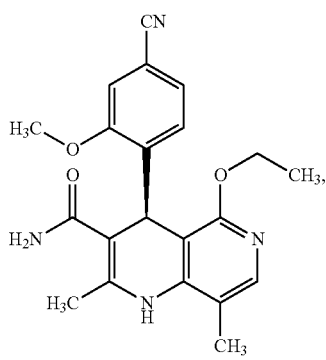

characterized in that the racemic acid of the formula (III)

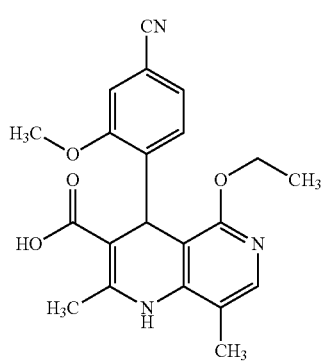

is reacted with halo esters of the general formula (V)

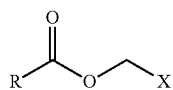

where
R is a linear or branched C1-C25 chain optionally substituted by an aromatic radical,
X is chlorine or bromine,
to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

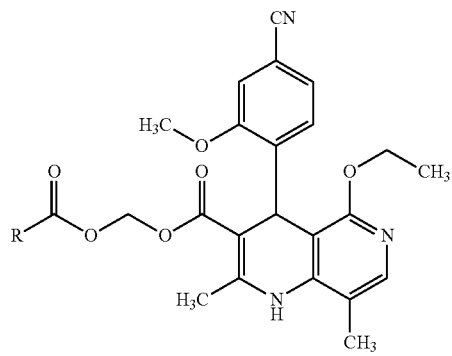

where R is a linear or branched C1-C25 chain optionally substituted by an aromatic radical,
and this is converted by optical resolution using
a hydrolase
to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

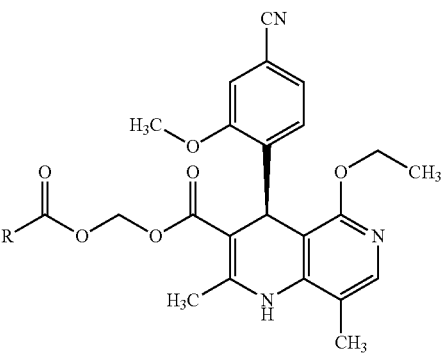

where R is a linear or branched C1-C25 chain optionally substituted by an aromatic radical,
and this is hydrolysed in a THF/water mixture (2:1) with sodium hydroxide solution to give the compound of the formula (IIIa)

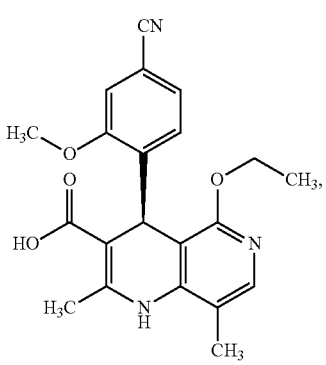

and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

7. Process according to paragraph 6, characterized in that
R is methyl, ethyl, n-propyl, isopropyl, tert-butyl, benzyl, n-butyl, n-pentyl or n-hexyl,
and
X is bromine.

8. Process according to paragraph 6 or 7, characterized in that
R is methyl,
and
X is bromine.

9. Process according to paragraph 6, 7 or 8, characterized in that lipase is used for the optical resolution.

10. Process according to paragraph 9, characterized in that AK lipase from *Pseudomonas fluorescens* is used for the optical resolution.

Paragraphs (1) to (27)

The following paragraphs (1) to (27) constitute further embodiments of the invention:

(1) Process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

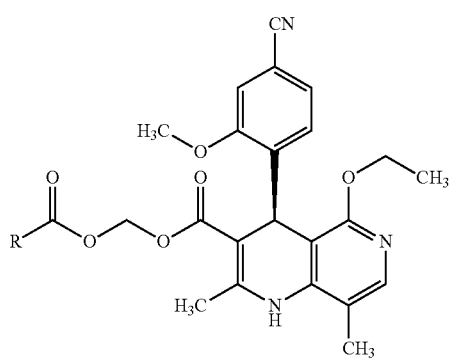

(IIa)

where R is a linear or branched C1-C25 chain optionally substituted by an aromatic radical, by optical resolution of (II)

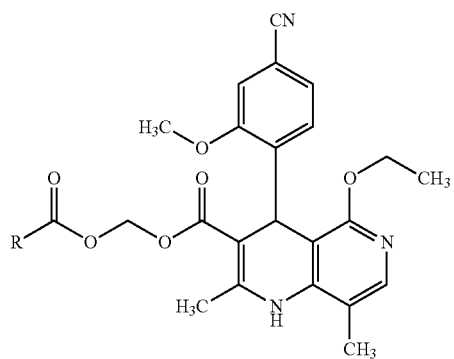

(II)

where R is a linear or branched C1-C25 chain optionally substituted by an aromatic radical, using a hydrolase.

(2) Process according to paragraph 1, wherein, in the compound of formula (IIa),
R is methyl, ethyl, n-propyl, isopropyl, tert-butyl, benzyl, n-butyl, n-pentyl or n-hexyl, and wherein, in the compound of formula (II),
R is methyl, ethyl, n-propyl, isopropyl, tert-butyl, benzyl, n-butyl, n-pentyl or n-hexyl.

(3) Process according to paragraph 1 or 2, wherein, in the compound of formula (IIa),
R is methyl, ethyl and isopropyl, n-butyl or n-pentyl, and wherein, in the compound of formula (II),
R is methyl, ethyl and isopropyl, n-butyl or n-pentyl.

(4) Process according to paragraph 1, 2 or 3, wherein, in the compound of formula (IIa),
R is methyl, and
wherein, in the compound of formula (II),
R is methyl.

(5) Process according to any of paragraphs 1 to 4, wherein the hydrolase used is a lipase.

(6) Process according to any of paragraphs 1 to 5, wherein the lipase is selected from type VII lipase from *Candida rugosa*, lipase from *Candida rugosa*, Amano lipase M from *Mucor javanicus*, Amano lipase PS from *Burkholderia cepacian*, Amano lipase PS-IM, lipase from *Aspergillus niger* lipase from *Thermomyces lanuginosus*, lipase from *Rhizomucor miehei*, lipase from *Candida antarctica* B, lipase from *Candida antarctica* A, lipase from *Aspergillus oryzae*, lipase from *Humicola insolens*, lipase from *Candida antarctica* B, lipase from *Thermomyces lanuginosus*, lipase from *Rhizomucor miehei*, lipase from *Candida antarctica* and lipase from porcine liver.

(7) Process according to any of paragraphs 1 to 6, wherein the lipase is AK lipase from *Pseudomonas fluorescens*.

(8) Process according to any of paragraphs 1 to 7, wherein the optical resolution is conducted in a monophasic system.

(9) Process according to any of paragraphs 1 to 7, wherein the optical resolution is conducted in a biphasic system.

(10) Process according to any of paragraphs 1 to 9, wherein the optical resolution is conducted in an aqueous buffer.

(11) Process according to any of paragraphs 1 to 10, wherein the optical resolution is conducted in an aqueous buffer selected from sodium phosphate, potassium phosphate and mixtures thereof.

(12) Process according to any of paragraphs 1 to 11, wherein the optical resolution is conducted at a pH between pH 7.0 and pH 10, between pH 7 and 8, or at pH 7.

(13) Process according to any of paragraphs 1 to 12, wherein the optical resolution is conducted in a water-miscible or -immiscible organic solvent.

(14) Process according to any of paragraphs 1 to 13, wherein the optical resolution is conducted in a water-miscible
organic solvent selected from the group consisting of ethanol, methanol, n-butanol, isopropanol, acetone, THF, DMF, DMSO, tert-butyl methyl ether, cyclopentyl methyl ether, 1,4-dioxane, 2-methyl-THF, toluene and mixtures thereof.

(15) Process according to any of paragraphs 1 to 14, wherein the optical resolution is conducted in a solvent combination selected from the group consisting of
2-methyl-THF/potassium phosphate buffer pH 7;
10% DMSO/90% 50 mM potassium phosphate buffer pH 7;
20% tert-butyl methyl ether/80% 50 mM potassium phosphate buffer pH 7;

water-saturated tert-butyl methyl ether/various buffers pH 7-pH 7.5;

50% cyclopentyl methyl ether/50% 50 mM K phosphate buffer pH 7;

1:1 w/w Triton X-100, 1.5% DMF/98.5% 50 mM potassium phosphate buffer pH 7-pH 8; and water-saturated 1,4-dioxane/various buffers pH 7-pH 7.5.

(16) Process for preparing (4S)-4-(4-cyano-2-methoxyphenyl)-5-ethoxy-2,8-dimethyl-1,4-dihydro-1,6-naphthyridine-3-carboxamide of the formula (Ia)

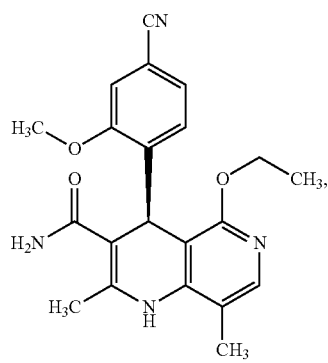

(Ia)

characterized in that the racemic acid of the formula (III)

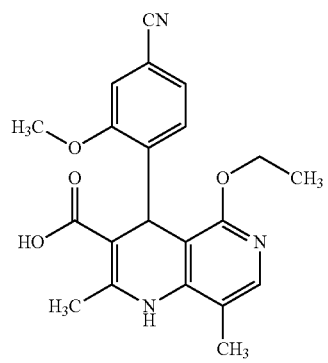

(III)

is reacted with halo esters of the general formula (V)

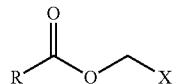

(V)

where

R is a linear or branched C1-C25 chain optionally substituted by an aromatic radical, X is chlorine or bromine, to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

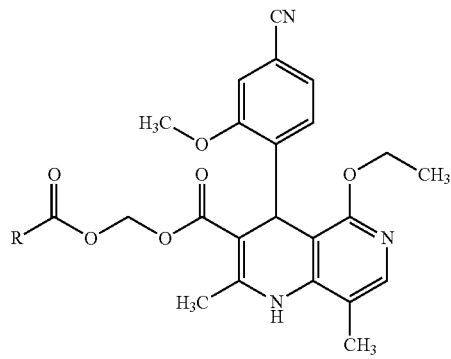

(II)

where R is a linear or branched C1-C25 chain optionally substituted by an aromatic radical, and this is converted by optical resolution using a hydrolase to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

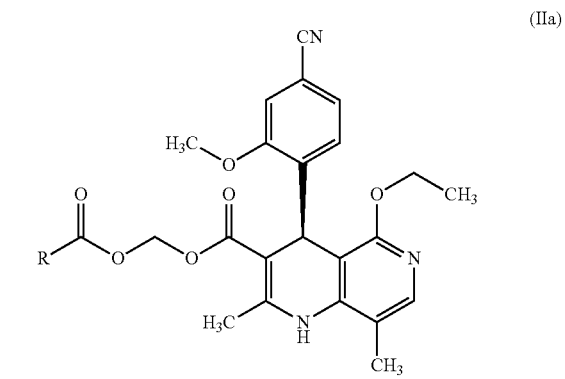

(IIa)

where R is a linear or branched C1-C25 chain optionally substituted by an aromatic radical, and this is hydrolysed in a THF/water mixture (2:1) with sodium hydroxide solution to give the compound of the formula (IIIa)

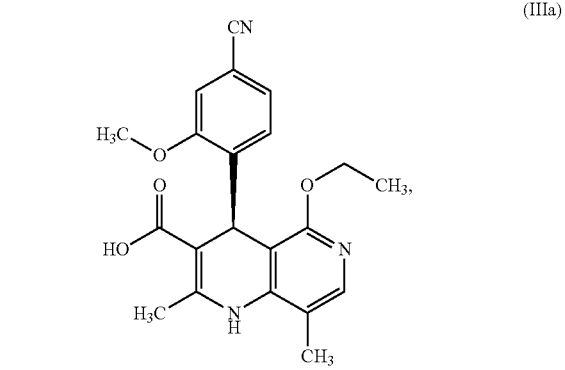 [SMILES: CCOc1ncc(C)c2c1[C@H](c1ccc(C#N)cc1OC)C(C(=O)O)=C(C)N2]

(IIIa)

and this compound of the formula (IIIa) is then reacted in THF as solvent firstly with 1,1-carbodiimidazole and catalytic amounts of 4-(dimethylamino)pyridine, hexamethyldisilazane is added and then the mixture is heated under reflux for 16-24 hours, and then a THF/water mixture is added.

(17) Process according to paragraph 16, wherein, in the compound of formula (V),
R is methyl, ethyl, n-propyl, isopropyl, tert-butyl, benzyl, n-butyl, n-pentyl or n-hexyl,
and
X is bromine,
and wherein, in the compound of formula (II),
R is methyl, ethyl, n-propyl, isopropyl, tert-butyl, benzyl, n-butyl or n-pentyl n-hexyl,
and wherein, in the compound of formula (IIa),
R is methyl, ethyl, n-propyl, isopropyl, tert-butyl, benzyl, n-butyl or n-pentyl.

(18) Process according to paragraph 16 or 17, wherein, in the compound of formula (V),
R is methyl, ethyl and isopropyl, n-butyl or n-pentyl,
and
X is bromine,
and wherein, in the compound of formula (II),
R is methyl, ethyl and isopropyl, n-butyl or n-pentyl,
and wherein, in the compound of formula (IIa),
R is methyl, ethyl and isopropyl, n-butyl or n-pentyl.

(19) Process according to any of paragraphs 16 to 18, wherein, in the compound of formula (V),
R is methyl,
and
X is bromine,
and wherein, in the compound of formula (II),
R is methyl,
and wherein, in the compound of formula (IIa),
R is methyl.

(20) Process according to any of paragraphs 8 to 11, wherein, in the formula (V), X is chlorine and R is as defined in any of paragraphs 16 to 19, and wherein, in the compound of formula (II), R is as defined in any of paragraphs 16 to 19, and wherein, in the compound of formula (IIa), R is as defined in any of paragraphs 16 to 19.

(21) Process according to any of paragraphs 16 to 20, wherein lipase is used for the optical resolution.

(22) Process according to any of paragraphs 16 to 21, wherein the lipase is selected from type VII lipase from *Candida rugosa*, lipase from *Candida rugosa*, Amano lipase M from *Mucor javanicus*, Amano lipase PS from *Burkholderia cepacian*, Amano lipase PS-IM, lipase from *Aspergillus niger* lipase from *Thermomyces lanuginosus*, lipase from *Rhizomucor miehei*, lipase from *Candida antarctica* B, lipase from *Candida antarctica* A, lipase from *Aspergillus oryzae*, lipase from *Humicola insolens*, lipase from *Candida antarctica* B, lipase from *Thermomyces lanuginosus*, lipase from *Rhizomucor miehei*, lipase from *Candida antarctica* and lipase from porcine liver.

(23) Process according to any of paragraphs 16 to 22, wherein the lipase is AK lipase from *Pseudomonas fluorescens*.

(24) Use of a hydrolase in a process for preparing a compound of formula (IIa) by optical resolution of the compound (II).

(25) Use according to paragraph 24, wherein the process for preparing the compound of formula (IIa) is as defined by any of paragraphs 1 to 15.

(25) Use of a hydrolase in a process for preparing a compound of formula (Ia).

(26) Use according to paragraph 25, wherein the process for preparing the compound of formula (Ia) is as defined by any of paragraphs 16 to 22.

(27) Use according to paragraph 25 or 26, wherein the process for preparing the compound of formula (Ia) is as defined by any of paragraphs 16 to 22, and also includes the process for preparing the compound of formula (IIa) as defined by any of paragraphs 1 to 15.

EXPERIMENTAL

Abbreviations and Acronyms

| | |
|---|---|
| EtOH | ethanol |
| DB tartaric acid | dibenzoyltartaric acid |
| DMSO | dimethyl sulfoxide |
| of th. | of theory (in yield) |
| HPLC | high-pressure, high-performance liquid chromatography |
| 1H-NMR | 1H nuclear magnetic resonance spectrometry |
| IT | internal temperature |
| MS | mass spectrometry |
| RT | room temperature |
| RRT | relative retention time |
| TFA | trifluoroacetic acid |
| TI | internal temperature |
| TM | jacket temperature |
| XRPD | X-ray powder diffraction (powder diffractometer) |
| Spirits | ethanol denatured with 2% toluene |

EXAMPLES

Table 3 below shows the structures of the compounds recovered in HPLC. The assignment of the retention times in HPLC is shown below.

TABLE 3

(Ia)

Finerenone

TABLE 3-continued
impurity A
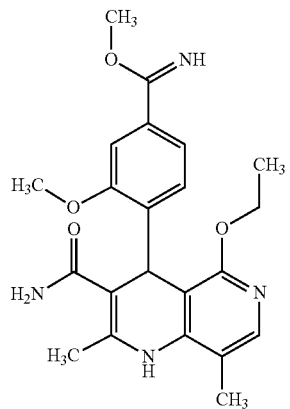 [SMILES: CCOc1ncc(C)c2c1C(c1ccc(C(=N)OC)cc1OC)C(C(N)=O)=C(C)N2]
impurity B
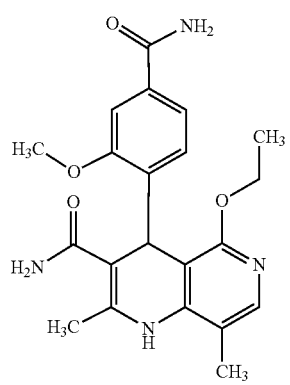 [SMILES: CCOc1ncc(C)c2c1C(c1ccc(C(N)=O)cc1OC)C(C(N)=O)=C(C)N2]
impurity C
(unknown structure, always significantly less than 0.1%)
impurity D
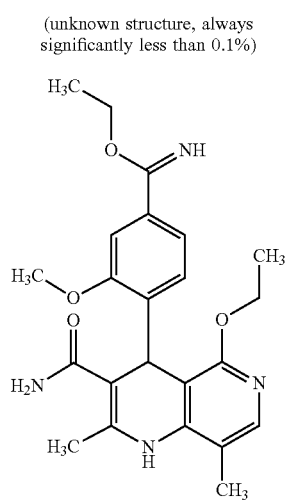
impurity E
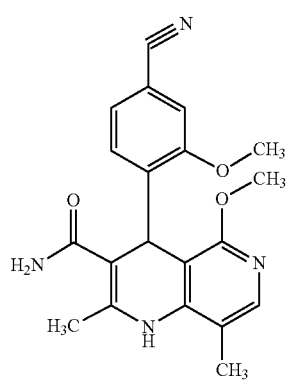 [SMILES: COc1cc(C#N)ccc1C1C(C(N)=O)=C(C)Nc2c(C)cnc(OC)c21]
TABLE 3-continued
impurity G
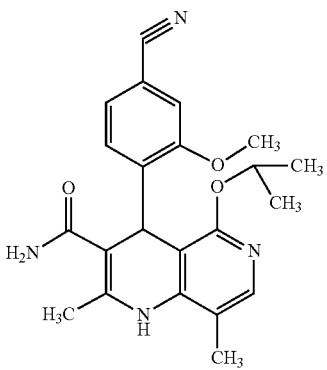 [SMILES: COc1cc(C#N)ccc1C1C(C(N)=O)=C(C)Nc2c(C)cnc(OC(C)C)c21]
impurity F
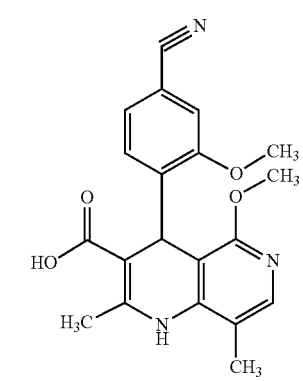 [SMILES: COc1cc(C#N)ccc1C1C(C(=O)O)=C(C)Nc2c(C)cnc(OC)c21]
impurity I
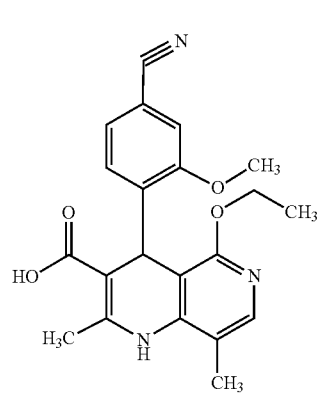 [SMILES: CCOc1ncc(C)c2c1C(c1ccc(C#N)cc1OC)C(C(=O)O)=C(C)N2]
impurity J
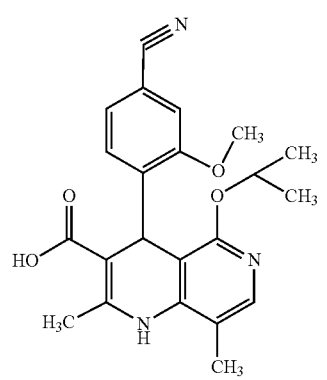 [SMILES: COc1cc(C#N)ccc1C1C(C(=O)O)=C(C)Nc2c(C)cnc(OC(C)C)c21]

TABLE 3-continued impurity K

[Chemical structure of impurity K: a compound with cyano group, methoxy, ethoxy, methyl groups, and carboxamide on a naphthyridine-like scaffold]

Analytical Method for Checking the Content of Impurities and the Enantiomeric Purity at the Stage of Crude Finerenone (Ia)

| Content and organic impurities | RT (min) | RRT |
|---|---|---|
| Finerenone (Ia) | 6.2 | 1.00 |
| impurity A | 3.3 | 0.53 |
| impurity B | 3.7 | 0.60 |
| impurity C | 3.9 | 0.62 |
| impurity D | 4.4 | 0.70 |
| impurity E | 5.5 | 0.89 |
| impurity F | 5.6 | 0.91 |
| impurity G | 6.8 | 1.10 |
| impurity H | 7.6 | 1.23 |
| impurity K | 10.4 | 1.68 |

Instrument: ultrahigh-performance liquid chromatograph (having a pressure range of up to 1200 bar with temperature-controlled column oven and UV detector)

Column: YMC Triart C8
  length: 100 mm; internal diameter: 3.0 mm; particle size: 1.9 µm
  Max pressure: 1000 bar Conditions: 20° C.; 0.50 ml/min; 1.7 µl (10° C.); 252 nm/6 nm and 230 nm/6 nm for the evaluation of DB tartaric acid Eluent: A: 0.1% TFA in water; B: acetonitrile Gradient: time (min) A (%) B (%)

| Enantiomeric purity: Method A | | |
|---|---|---|
| | RT (min) | RRT |
| Finerenone (Ia) | about 11 | 1.00 |
| (Ia) | about 9 | 0.82 |

Instrument: high-performance liquid chromatograph with temperature-controlled column oven and UV detector Column: Chiralpak IA
  length: 250 mm, internal diameter: 4.6 mm, particle size: 5.0 µm
  Max pressure: 300 bar Conditions: 40° C.; 0.8 ml/min; 5 µl (20° C.); 255 nm/6 nm Eluent: A: acetonitrile; B: methyl tert-butyl ether (MTBE)
Isocratic: A(%) 90: B(%) 10

Enantiomeric Purity

| Method B | | |
|---|---|---|
| | RT(min) | RRT |
| Finerenone (Ia) | 5.7 | 1.00 |
| Enantiomer (Ib) | 6.8 | 1.19 |

Instrument/detector: high-performance liquid chromatograph with temperature-controlled column oven, UV detector
and data evaluation system Measurement wavelength: 252 nm
Oven temperature: 40° C.
Column: Chiralpak IC
  length: 150 mm, internal diameter: 4.6 mm, particle size: 3 µm
Mobile phase:
A: 50% buffer 20 mM $NH_4OAc$ pH 9
B: 50% acetonitrile
Flow rate: 1 ml/min.
Elution time: 8 min.
Equilibration: unnecessary, isocratic
Sample solvent: eluent
Sample solution: about 0.5 mg/ml of the substance racemate, dissolved in sample solvent
Comparative solution: A comparative solution analogous to the sample solution is prepared
Injection volume: 10 µl The measured values stated in the examples below for enantiomer determination were all determined by Method B. Some values, especially those of the batches prepared in the pilot plant, were reanalysed with Method A for comparison, and gave comparable results.

The HPLC analysis data given in the examples which follow with respect to purity and content of the end product pure finerenone (Ia) relate solely to impurities present in the product in an amount of >0.05%. This is essentially impurity E. All other impurities shown in the table listed above are generally <0.05%. The structure of such impurities was determined by isolation from enriched mother liquors.

HPLC Conditions/Methods
Method (C)
  YMC Hydrosphere C18
  150*4.6 mm, 3.0 µm
  25° C., 1 ml/min, 270 nm, 4 nm
  0': 70% TFA 0.1%*; 30% acetonitrile
  17': 20% TFA 0.1%; 80% acetonitrile
  18': 70% TFA 0.1%; 30% acetonitrile
  *: TFA in water
Method (D)
  YMC Hydrosphere C18
  150*4.6 mm, 3.0 m
  25° C., 1 ml/min, 255 nm, 6 nm
  0': 90% TFA 0.1%; 10% acetonitrile
  20': 10% TFA 0.1%; 90% acetonitrile
  18': 10% TFA 0.1%; 90% acetonitrile
Method (E)
  Nucleodur Gravity C18
  150*2 mm, 3.0 m
  35° C., 0.22 ml/min, 255 nm, 6 nm Solution A: 0.58 g of ammonium hydrogenphosphate and 0.66 g of ammonium dihydrogenphosphate in 1 l of water (ammonium phosphate buffer pH 7.2)

Solution B: acetonitrile

0': 30% B; 70% A
15': 80% B; 20% A
25': 80% B; 20% A

Method (F)

Column: Nucleodur C18 Gravity, 50×3 mm, 1.8 µm, 45° C., 1.2 m/min, 210 nm, 1.2 nm;
Solvent A: aqueous 0.1% formic acid solution
Solvent B: acetonitrile 0.1% formic acid solution
0': 80% A; 20% B
1.3': 20% A; 80% B
2': 20% A; 80% B
2.5': 80% A; 20% B

| Method (G) | | |
| --- | --- | --- |
| | RT(min) | RRT |
| Acyloxymethyl ester (IIAa) | about 9.9 | 1.00 |
| Acyloxymethyl ester (IIAb) | about 11.4 | 1.15 |

Column: Chiralpak AD-H, 250×4.6 mm, 5 µm, 40° C., 2 ml/min, 207 nm. 6 nm:
Solvent A: n-heptane
Solvent B: ethanol+0.1% diethylamine solution
0': 95% A; 5% B
16': 95% A; 5% B
16.1': 10% A; 90% B
20': 10% A; 90% B
Equilibration: 10 min Example 1

In parallel synthesis equipment, the following racemic acyloxy esters of the general formula (II) were synthesized in 10-15 mg* and characterized via mass spectrometry:

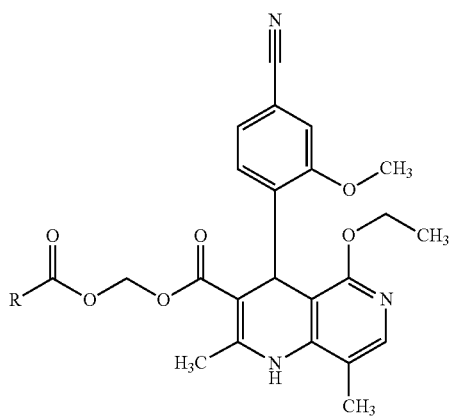

(II)

| II (A-F) | RCOOCH$_2$Br (V A-F) R | R | [M + H]$^+$ | Amount (mg) |
| --- | --- | --- | --- | --- |
| A | methyl | methyl | 452 | 13 |
| B | ethyl | ethyl | 466 | 12 |
| C | n-propyl | n-propyl | 480 | 15 |
| D | i-propyl | i-propyl | 480 | 10 |
| E | n-butyl | n-butyl | 494 | 11 |
| F | n-pentyl | n-pentyl | 508 | 13 |

*Acid (III) was stirred together with a bromo ester (V A-F)) in DMF and potassium carbonate at 40° C. The solids were filtered off, and the filtrate was chromatographed directly for purification and then isolated by freeze-drying.

Example 2

Screening Results

For the kinetic separation of the racemic acyloxy esters (II A-F), the potential of multiple hydrolases was tested. The racemic starting material was dissolved in an organic solvent such as DMSO, tert-butyl methyl ether, cyclopentyl methyl ether, 1,4-dioxane, DMF or 2-methyl-THF, and added above a buffered aqueous solution (pH 7) of an enzyme. The following lipases were used: AK lipase from *Pseudomonas fluorescens*, type VII lipase from *Candida rugosa*, lipase from *Candida rugosa*, Amano Lipase M, from *Mucor javanicus*, Amano Lipase PS, from *Burkholderia cepacia*, Amano Lipase PS-IM, lipase from *Aspergillus niger*, lipase from *Thermomyces lanuginosus*, lipase from *Rhizomucor miehei*, lipase from *Candida antarctica* B, lipase from *Candida antarctica* A, lipase from *Aspergillus oryzae*, lipase from *Humicola insolens*, lipase from *Candida antarctica* B, immobilized, lipase from *Thermomyces lanuginosus* (immobilized), lipase from *Rhizomucor miehei* (immobilized), lipase from *Candida antarctica* in acrylic resin or lipase from porcine liver. The resulting biphasic system was stirred at 22 to 36° C. until a conversion level of nearly 50% had been attained. The separation of the product and of the enantiomerically purified substrate was conducted by means of base-acid extraction. The treatment of the organic layer with 5% aqueous potassium phosphate solution separates the desired enantiomerically purified residual ester from the acid, and conducts a chromatographic determination of enantiomeric excess (Method G).

The enantiomeric excesses (ee) achieved are generally between 70% e.e. and 91% e.e.; the 4R enantiomer is preferentially hydrolysed.

For further upscaling of the reaction, (f)-acetoxymethyl 4-(4-cyano-2-methoxyphenyl)-5-ethoxy-2,8-dimethyl-1,4-dihydro-1,6-naphthyridine-3-carboxylate (IIA) was selected, since it showed the best results in the screening.

In principle, the other esters (II B-F) would also be suitable for suitable upscaling.

Example 3a

Acetoxymethyl (4S,4R)-4-(4-cyano-2-methoxyphenyl)-5-ethoxy-2,8-dimethyl-1,4-dihydro-1,6-naphthyridine-3-carboxylate (IIA)

An initial charge of 57.68 g (152.024 mmol) of racemic (4S,4R)-(4-cyano-2-methoxyphenyl)-5-ethoxy-2,8-dimethyl-1,4-dihydro-1,6-naphthyridine-3-carboxylic acid (III), 46.51 g (304.049 mmol) of bromomethyl acetate (VA) and 42.02 g (304.05 mmol) of potassium carbonate in 288 ml of dimethylacetamide was stirred at 20° C. for 20 h (full conversion by TLC, ethyl acetate/heptane 1:1, R$_f$(ester=0.18)). The reaction mixture is filtered (removal of the salts), and the filter residue is washed with 400 ml of ethyl acetate. The filtrate is washed twice with 400 ml of water and then with 200 ml of saturated aqueous sodium chloride solution. The organic phase is concentrated to dryness under reduced pressure, and the residue is recrystallized from 200 ml of tert-butyl methyl ether/50 ml of ethanol.

Yield: 27.04 g (39% of theory), it was possible to isolate a further 20 g of material from the mother liquor.

MS (ES+): 452 [M+H]$^+$, $^1$H-NMR (500 MHz, DMSO-d$_6$): δ=1.10 (t, J=7.09 Hz, 3H), 1.96 (s, 3H), 2.16 (s, 3H), 2.42 (s, 3H), 3.75 (s, 3H), 3.99-4.11 (m, 2H), 5.32 (s, 1H), 5.56-5.64 (m, 2H), 7.21-7.27 (m, 2H), 7.31 (s, 1H), 7.61 (s, 1H), 8.50 (s, 1H) ppm.

Example 3b

Acetoxymethyl (4S)-4-(4-cyano-2-methoxyphenyl)-5-ethoxy-2,8-dimethyl-1,4-dihydro-1,6-naphthyridine-3-carboxylate (IIa: R=Me))

A 6 l jacketed glass reactor was initially charged with AK lipase from *Pseudomonas fluorescens* (22.5 g, 21 000 U/g), potassium phosphate buffer (2.1 l, 50 mM, pH 7.0) and a solution of racemic (±)-acetoxymethyl (4S,4R)-4-(4-cyano-2-methoxyphenyl)-5-ethoxy-2,8-dimethyl-1,4-dihydro-1,6-naphthyridine-3-carboxylate (IIA) (15 g, 33.224 mmol) in 2-methyltetrahydrofuran (2-Me-THF, 0.9 l). The resulting biphasic mixture was stirred at 28.5° C. and 110 rpm (emulsion) for 7 days. Additional amounts of enzyme were added after 2, 3 and 4 days to give a total of 45 g (1:3 wt./wt. substrate/enzyme). After a conversion of 55% (enantiomerically enriched ester (IIa: R=Me; 92% ee)), the reaction was stopped by adding sodium chloride (150 g) and extracted with 2-MeTHF (2×1 l). The organic phases were combined with 2 l of a 5% potassium phosphate solution at 0° C. and stirred for 40 min. The organic phase was removed, dried with sodium sulfate, filtered and concentrated to dryness under reduced pressure.

An orange oil was obtained (8.34 g). The crude reaction product was purified by flash chromatography on silica gel using a solvent gradient (15% EtOAc/heptane-100% EtOAc). This gives 4.78 g (32% of theory) of a white solid.

Enantiomeric excess: 91% e.e. (Method G)

$t_R$ (HPLC Method F): 1.1 min;

MS (ES+): 452 [M+H]$^+$, $^1$H-NMR (500 MHz, DMSO-d$_6$): δ=1.10 (t, J=7.09 Hz, 3H), 1.96 (s, 3H), 2.16 (s, 3H), 2.42 (s, 3H), 3.75 (s, 3H), 3.99-4.10 (m, 2H), 5.31 (s, 1H), 5.56-5.64 (m, 2H), 7.21-7.28 (m, 2H), 7.31 (s, 1H), 7.61 (s, 1H), 8.49 (s, 1H) ppm.

10 batches proceeding from 15 g of racemic (±)-acetoxymethyl (4S,4R)-4-(4-cyano-2-methoxyphenyl)-5-ethoxy-2,8-dimethyl-1,4-dihydro-1,6-naphthyridine-3-carboxylate (IIA) were enzymatically hydrolysed, and the crude products were combined. This gave 46 g of material with 91% e.e. This crude product was recrystallized from 120 ml of tert-butyl methyl ether/30 ml of ethanol, and 41 g of the optically pure ester (IIa: R=Me; e.e.%>99%) was obtained.

This material was converted to finerenone (Ia) in analogy to the processes described in WO 2016/016287 A1. This is described in the examples that follow.

Example 3c (4S)-(4-Cyano-2-methoxyphenyl)-5-ethoxy-2,8-dimethyl-1,4-dihydro-1,6-naphthyridine-3-carboxylic acid (IIIa)

40.0 g (88.69 mmol) of acetoxymethyl (4S)-4-(4-cyano-2-methoxyphenyl)-5-ethoxy-2,8-dimethyl-1,4-dihydro-1,6-naphthyridine-3-carboxylate (IIa: R=Me)) was dissolved in a mixture of 240 ml of THF and 120 ml of water, and cooled down to 0° C. To this solution was added dropwise, at 0° C. within 15 minutes, a sodium hydroxide solution (prepared from 16.4 g (184.96 mmol) of 45% aqueous sodium hydroxide solution and 85 ml of water), and the mixture was stirred at 0° C. for 1.5 hours. The mixture was extracted twice with 100 ml each time of methyl tert-butyl ether and once with 100 ml of ethyl acetate. The aqueous solution at 0° C. was adjusted to pH 7 with dilute hydrochloric acid (prepared from 37.1 g of 37% HCl and 151 ml of water). The solution was allowed to warm up to 20° C., and an aqueous solution of 41 g of ammonium chloride in 110 ml of water was added. The solution was stirred at 20° C. for 1 hour, and the product was filtered off and washed twice with 30 ml each time of water and once with 80 ml of acetonitrile. The product was dried at 40° C. under vacuum under entraining gas.

Yield: 30.6 g (91.0% of theory) of an almost colourless powder (very slight yellow tint).

HPLC Method E: RT: about 6.8 min.

MS (EIpos): m/z=380 [M+H]$^+$ $^1$H-NMR (300 MHz, DMSO-d$_6$): δ=1.14 (t, 3H), 2.14 (s, 3H), 2.37 (s, 3H), 3.73 (s, 3H), 4.04 (m, 2H), 5.33 (s, 1H), 7.26 (m, 2H), 7.32 (s, 1H), 7.57 (s, 1H), 8.16 (s, 1H), 11.43 (br. s, 1H).

Example 3d (4S)-4-(4-Cyano-2-methoxyphenyl)-5-ethoxy-2,8-dimethyl-1,4-dihydro-1,6-naphthyridine-3-carboxamide (Ia)

To an initial charge of 30 g (79.13 mmol) of (4S)-(4-cyano-2-methoxyphenyl)-5-ethoxy-2,8-dimethyl-1,4-dihydro-1,6-naphthyridine-3-carboxylic acid (IIIa) and 17.96 g (110.8 mmol) of 1,1-carbodiimidazole in 150 ml of THF was added 956 mg (7.82 mmol) of DMAP at 20° C. The mixture was stirred at 20° C. for one hour (evolution of gas!) and then heated to 50° C. for 2.5 hours. 55.7 g (0.345 mol) of hexamethyldisilazane was added to this solution, which was boiled under reflux for 22 hours. A further 34 ml of THF was added and the mixture was cooled to 5° C. A mixture of 22 ml of THF and 15.7 g of water was added over 3 hours such that the temperature remained between 5 and 20° C. The mixture was subsequently boiled under reflux for one hour, then cooled via a gradient (3 hours) to 0° C. and stirred at that temperature for one hour. The product was filtered off and washed twice with 38 ml each time of THF and twice with 60 ml each time of water. The product was dried at 70° C. under vacuum under entraining gas.

Yield: 27.67 g (92.5% of theory) of an almost colourless powder (very slight yellow tint).

HPLC method D: RT about 6.7 min.

MS (EIpos): m/z=379 [M+H]$^+$ $^1$H-NMR (300 MHz, DMSO-d$_6$): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m, 2H), 7.14 (d, 1H), 7.28 (dd, 1H), 7.37 (d, 1H), 7.55 (s, 1H), 7.69 (s, 1H).

Example 3e

Preparation of Pure Product (Ia=Finerenone)

27.0 g of the crude product (Ia) prepared in Example 3d was suspended in 540 ml of ethanol (denatured with toluene) and then heated to reflux. On heating, the product went into solution. Stirring was continued at this temperature for one hour. The solution was filtered off through a heated pressure filter (T=75° C.) and the pressure filter was then rinsed with 7 ml of ethanol (denatured with toluene). The solvent was then distilled off (about 444 ml was distilled off) until a final volume of about 4 times the substance used (27.0 g×4~110 ml) had been attained. The mixture was then cooled to internal temperature 23° C. (over about 1.5 to 2 hours). The mixture was then stirred at internal temperature 3° C. for 2 hours. The product was filtered off and rinsed once with 100 ml of ethanol (denatured with toluene). Wet yield: 28 g. The wet product was dried at 50° C. over the weekend (>48 h) under reduced pressure (<100 mbar). Yield: 25.67 g (95.1% of theory) of a colourless crystalline powder, fine needle-like crystals.

Analytical Results:

| | |
|---|---|
| Finerenone (Ia) | Purity: 99.85 area (HPLC); Content: 99.7% by weight |
| Enantiomeric excess | 100% e.e. |
| Largest secondary component impurity E | 0.05% |
| Residual solvents: | |
| EtOH | 0.05% |
| toluene | 0.00% |
| water (Karl Fischer) | 0.00% |

MS (EIpos): m/z=379 [M+H]$^+$ $^1$H-NMR (400 MHz, DMSO-d$_6$): δ=1.05 (t, 3H), 2.12 (s, 3H), 2.18 (s, 3H), 3.82 (s, 3H), 3.99-4.07 (m, 2H), 5.37 (s, 1H), 6.60-6.84 (m (broad signal), 2H), 7.14 (d, 1H), 7.28 (dd, 1H), 7.37 (d, 1H), 7.55 (s, 1H), 7.69 (s, 1H) and small signals of the DMSO solvent and water at δ=2.5-2.6 and a very small peak at δ=3.38 (not assignable)

Modification: Mod A (as defined in WO2016/016287 A1)

The invention claimed is:

1. A process for preparing acyloxymethyl esters of (4S)-(4-cyano-2-methoxyphenyl)-5-ethoxy-2,8-dimethyl-1,4-dihydro-1,6-naphthyridine-3-carboxylic acid of the formula (IIa)

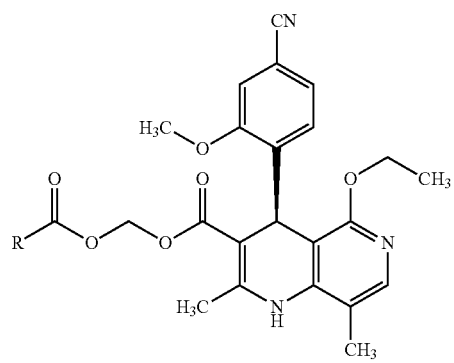

(IIa)

where R is a linear or branched C1-C25 chain optionally substituted by an aromatic radical, comprising converting the compound of the formula (II)

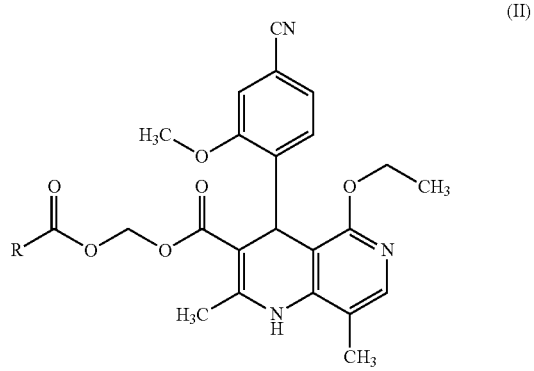

(II)

where R is a linear or branched C1-C25 chain optionally substituted by an aromatic radical, by optical resolution using a hydrolase.

2. Process according to claim 1, wherein, in the compound of formula (IIa),

R is methyl, ethyl, n-propyl, isopropyl, tert-butyl, benzyl, n-butyl, n-pentyl or n-hexyl, and wherein, in the compound of formula (II), R is methyl, ethyl, n-propyl, isopropyl, tert-butyl, benzyl, n-butyl, n-pentyl or n-hexyl.

3. Process according to claim 1, wherein, in the compound of formula (IIa),

R is methyl, and wherein, in the compound of formula (II),

R is methyl.

4. Process according to claim 1, wherein the hydrolase used is a lipase, esterase, amidase or protease.

5. Process according to claim 1, wherein the hydrolase is a lipase.

6. Process according to claim 5, wherein the lipase is selected from type VII lipase from *Candida rugosa*, lipase from *Candida rugosa*, Amano lipase M from *Mucor javanicus*, Amano lipase PS from *Burkholderia cepacian*, Amano lipase PS-IM, lipase from *Aspergillus niger* lipase from *Thermomyces lanuginosus*, lipase from *Rhizomucor miehei*, lipase from *Candida antarctica* B, lipase from *Candida antarctica* A, lipase from *Aspergillus oryzae*, lipase from *Humicola insolens*, lipase from *Candida antarctica* B, lipase from *Thermomyces lanuginosus*, lipase from *Rhizomucor miehei*, lipase from *Candida antarctica* and lipase from porcine liver.

7. Process according to claim 5, wherein the lipase is AK lipase from *Pseudomonas fluorescens*.

8. A process for preparing (4S)-4-(4-cyano-2-methoxyphenyl)-5-ethoxy-2,8-dimethyl-1,4-dihydro-1,6-naphthyridine-3-carboxamide of the formula (Ia)

(Ia)

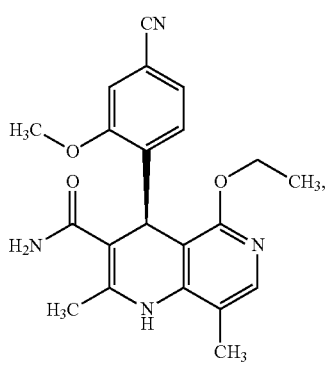

comprising reacting a racemic acid of the formula (III)

(III)

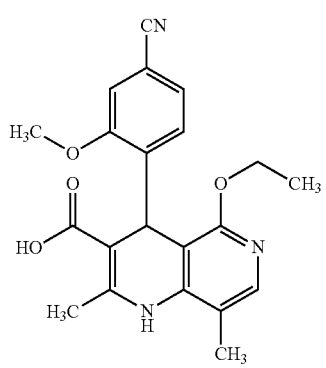

with halo esters of the general formula (V)

(V)

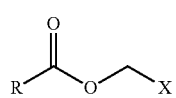

where
R is a linear or branched C1-C25 chain optionally substituted by an aromatic radical,
X is chlorine or bromine,
to give racemic acyloxymethyl esters of (4S)-(4-cyano-2-methoxyphenyl)-5-ethoxy-2,8-dimethyl-1,4-dihydro-1,6-naphthyridine-3-carboxylic acid of the formula (II)

(II)

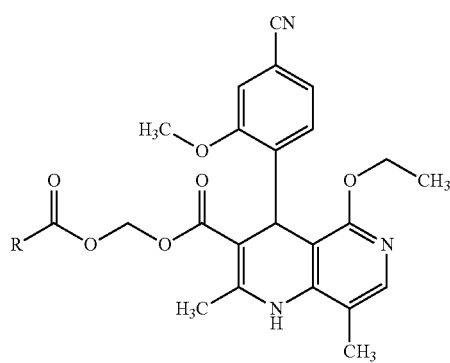

where R is a linear or branched C1-C25 chain optionally substituted by an aromatic radical, converting the compound of the formula (II) by optical resolution using a hydrolase to the enantiomeric acyloxymethyl ester of (4S)-(4-cyano-2-methoxyphenyl)-5-ethoxy-2,8-dimethyl-1,4-dihydro-1,6-naphthyridine-3-carboxylic acid of the formula (IIa)

(IIa)

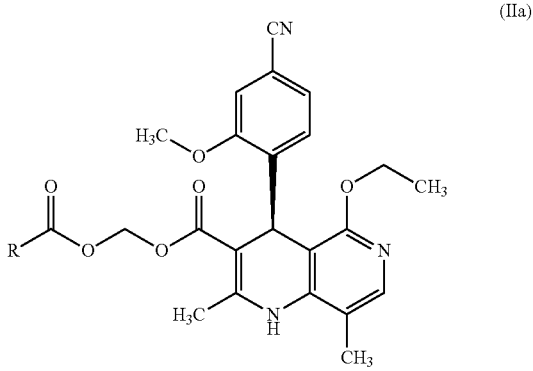

where R is a linear or branched C1-C25 chain optionally substituted by an aromatic radical, hydrolysing the compound of the formula (IIa) in a THF/water mixture (2:1) with sodium hydroxide solution to give the compound of the formula (IIIa)

(IIIa)

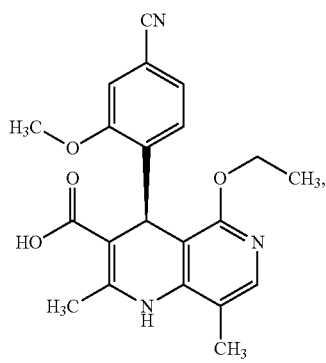

reacting the compound of the formula (IIIa) in THF as solvent firstly with 1,1-carbodiimidazole and catalytic amounts of 4-(dimethylamino)pyridine, then adding hexamethyldisilazane to form a mixture and heating the mixture under reflux for 16-24 hours,
and then adding a THF/water mixture.

9. Process according to claim 8, wherein, in the compound of formula (V),
R is methyl, ethyl, n-propyl, isopropyl, tert-butyl, benzyl, n-butyl, n-pentyl or n-hexyl,
and
X is bromine,
and wherein, in the compound of formula (II),
R is methyl, ethyl, n-propyl, isopropyl, tert-butyl, benzyl, n-butyl or n-pentyl n-hexyl,
and wherein, in the compound of formula (IIa),
R is methyl, ethyl, n-propyl, isopropyl, tert-butyl, benzyl, n-butyl or n-pentyl.

10. Process according to claim 8, wherein, in the compound of formula (V),
R is methyl, ethyl and isopropyl, n-butyl or n-pentyl, and
X is bromine,
and wherein, in the compound of formula (II),
R is methyl, ethyl and isopropyl, n-butyl or n-pentyl,
and wherein, in the compound of formula (IIa),
R is methyl, ethyl and isopropyl, n-butyl or n-pentyl.

11. Process according to claim 8, wherein, in the compound of formula (V),
R is methyl,
and
X is bromine,
and wherein, in the compound of formula (II),
R is methyl,
and wherein, in the compound of formula (IIa),
R is methyl.

12. Process according to claim 8, wherein, in the formula (V),
X is chlorine.

13. Process according to claim 8, wherein, for the optical resolution, a lipase is used.

14. The process of claim 13, wherein the lipase is selected from the group consisting of type VII lipase from *Candida rugosa*, lipase from *Candida rugosa*, Amano lipase M from *Mucor javanicus*, Amano lipase PS from *Burkholderia cepacian*, Amano lipase PS-IM, lipase from *Aspergillus niger* lipase from *Thermomyces lanuginosus*, lipase from *Rhizomucor miehei*, lipase from *Candida antarctica* B, lipase from *Candida antarctica* A, lipase from *Aspergillus oryzae*, lipase from *Humicola insolens*, lipase from *Candida antarctica* B, lipase from *Thermomyces lanuginosus*, lipase from *Rhizomucor miehei*, lipase from *Candida antarctica* and lipase from porcine liver.

15. The process of claim 13, wherein the lipase is AK lipase from *Pseudomonas fluorescens*.

\* \* \* \* \*